United States Patent
Adler-Abramovich et al.

(10) Patent No.: US 12,123,018 B2
(45) Date of Patent: Oct. 22, 2024

(54) SELF-ASSEMBLED HYBRID HYDROGELS FORMED OF A SHORT AROMATIC PEPTIDE AND AN AROMATIC AMINO ACID

(71) Applicant: Ramot at Tel-Aviv University Ltd., Tel-Aviv (IL)

(72) Inventors: Lihi Adler-Abramovich, Tel-Aviv (IL); Rina Sevostianov, Tel-Aviv (IL); Irena Grigoriants, Tel-Aviv (IL); Ehud Gazit, Tel-Aviv (IL)

(73) Assignee: Ramot at Tel-Aviv University Ltd., Tel-Aviv (IL)

(*) Notice: Subject to any disclaimer, the term of this patent is extended or adjusted under 35 U.S.C. 154(b) by 503 days.

(21) Appl. No.: 16/630,498

(22) PCT Filed: Jul. 13, 2018

(86) PCT No.: PCT/IL2018/050773
§ 371 (c)(1),
(2) Date: Jan. 13, 2020

(87) PCT Pub. No.: WO2019/012545
PCT Pub. Date: Jan. 17, 2019

(65) Prior Publication Data
US 2020/0165565 A1      May 28, 2020

Related U.S. Application Data

(60) Provisional application No. 62/531,905, filed on Jul. 13, 2017.

(51) Int. Cl.
*C12N 5/00* (2006.01)

(52) U.S. Cl.
CPC ........ *C12N 5/0062* (2013.01); *C12N 2513/00* (2013.01); *C12N 2533/20* (2013.01); *C12N 2535/00* (2013.01)

(58) Field of Classification Search
None
See application file for complete search history.

(56) References Cited

U.S. PATENT DOCUMENTS

2009/0175785 A1* 7/2009 Gazit ................ A61L 27/227
                                                              424/9.1
2011/0300767 A1   12/2011 Gedanken et al.
(Continued)

FOREIGN PATENT DOCUMENTS

EP      2294260       3/2011
EP      2839070       2/2015
(Continued)

OTHER PUBLICATIONS

Ryan et al., Langmuir 2011, 27, 1145-11156 (Year: 2011).*
(Continued)

*Primary Examiner* — Evelyn Y Pyla
*Assistant Examiner* — E. Y Pyla

(57) ABSTRACT

Hybrid hydrogels, made of a three-dimensional network of fibrillar nanostructures, at least a portion of the fibrillar nanostructures being formed of at least two different types of aromatic moieties, at least one type of the aromatic moieties being an end-capping modified aromatic dipeptide and at least another type of the aromatic moieties being an amine-modified halogenated aromatic amino acid, are provided. Also provided are processes of preparing the hybrid hydrogels and uses thereof.

15 Claims, 8 Drawing Sheets

(56) References Cited

U.S. PATENT DOCUMENTS

2016/0326215 A1 11/2016 Marcu et al.
2021/0030918 A1 2/2021 Adler-Abramovich et al.

FOREIGN PATENT DOCUMENTS

| WO | WO 2004/052773 | 6/2004 |
| WO | WO 2004/060791 | 7/2004 |
| WO | WO 2007/043048 | 4/2007 |
| WO | WO 2014/132262 | 9/2014 |
| WO | WO 2014/178057 | 11/2014 |
| WO | WO 2017/068584 | 4/2017 |
| WO | WO 2019/012545 | 1/2019 |

OTHER PUBLICATIONS

Official Action Dated May 10, 2022 from US Patent and Trademark Office Re. U.S. Appl. No. 16/942,837. (16 pages).
Interview Summary Dated Feb. 11, 2022 from US Patent and Trademark Office Re. U.S. Appl. No. 16/942,837. (2 pages).
Zhao et al. "Self-Assembling Peptide-Based Nanoarchitectonics", Bulletin of Chemical Society of Japan, 92(1): 70-79, 2019.
International Search Report and the Written Opinion Dated Oct. 22, 2018 From the International Searching Authority Re. Application No. PCT/IL2018/050773. (10 Pages).
Abramov et al. "Pilot Scale Sonochemical Coating of Nanoparticles Onto Textiles to Produce Biocidal Fabrics", Surface & Coatings Technology, 204(5): 718-722, Available Online Sep. 17, 2009.
Adler-Abramovich et al. "Controlled Patterning of Peptide Nanotubes and Nanospheres Using Inkjet Printing Technology", Journal of Peptide Science, 14: 217-223, Published Online Nov. 26, 2007.
Adler-Abramovich et al. "Controlling the Physical Dimensions of Peptide Nanotubes by Supramolecular Polymer Coassembly", ACS Nano, 10 (8): 7436-7442, 2016.
Adler-Abramovich et al. "Phenylalanine Assembly Into Toxic Fibrils Suggests Amyloid Etiology in Phenylketonuria", Nature Chemical Biology, XP002678189, 8: 701-706, Published Online Jun. 17, 2012.
Adler-Abramovich et al. "The Physical Properties of Supramolecular Peptide Assemblies: From Building Block Association to Technological Applications", Chemical Society Reviews, 43(20): 6881-6893, Oct. 21, 2014.
Burch et al. "N-(Fluorenyl-9-Methoxycarbonyl) Amino Acids, A Class of Antiinflammatory Agents With A Different Mechanism of Action", Proc. Natl. Acad. Sci. USA, 88(2): 355-359, Jan. 15, 1991.
Carny et al. "Fabrication of Coaxial Metal Nanocables Using A Self-Assembled Peptide Nanotube Scaffold", Nano Letters, 6(8): 1594-1597, Published on Web Jul. 7, 2006.
Cheng et al. "One-Step Synthesis of the Nanostructured AgI/BiOI Composites with Highly Enhanced Visible-Light Photocatalytic Performances", Langmuir, 26 (9): 6618-6624, 2010.
Draper et al. "Hydrogels Formed From Fmoc Amino Acids", CrystEngComm, 17(42): 8047-8057, Jun. 11, 2015.
Dudukovic et al. "Mechanical Properties of Self-Assembled Fmoc-Diphenylalanine Molecular Gels", Langmuir, 30 (15): 4493-4500, 2014.
Fichman et al. "Synergetic Functional Properties of Two-Component Single Amino Acid-Based Hydrogels", CrystEngComm, 17(42): 8105-8112, Published Online Jul. 17, 2015.
Gelain et al. "BMHP1-Derived Self-Assembling Peptides: Hierarchically Assembled Structures With Self-Healing Propensity and Potential for Tissue Engineering Applications", ACS Nano, 5(3): 1845-1859, Published Online Feb. 11, 2011.
Ghosh et al. "Templated Growth of Hybrid Structures at the Peptide-Peptide Interface", Chemistry: A European Journal, 14: 1415-1419, 2008.
Halperin-Sternfeld et al. "Molecular Co-Assembly as A Strategy for Synergistic Improvement of the Mechanical Properties of Hydrogels", ChemComm, 53(69): 9586-9589, Aug. 24, 2017.
Jayawarna et al. "Introducing Chemical Functionality in Fmoc-Peptide Gels for Cell Culture", Acta Biomaterialia, 5(3): 934-943, Available Online Jan. 18, 2009.
Jayawarna et al. "Nanostructured Hydrogels for Three-Dimensional Cell Culture Through Self-Assembly of Fluorenylmethoxycarbonyl-Dipeptides", Advanced Materials, 18(5): 611-614, Mar. 3, 2006.
Li et al. "D-Amino Acids Boost the Selectivity and Confer Supramolecular Hydrogels of A Non-Steroidal Anti-Inflammatory Drug (NSAID)", Journal of the American Chemical Society, 135(2): 542-545, Jan. 16, 2013.
Loo et al. "Peptide Bioink: Self-Assembling Nanofibrous Scaffolds for Three-Dimensional Organotypic Cultures", Nano Letters 15 (10): 6919-6925, 2015.
Mahler et al. "Rigid, Self-Assembled Hydrogel Composed of A Modified Aromatic Dipeptide", Advanced Materials, XP002446150, 18(11): 1365-1370, Apr. 25, 2006.
Maity et al. "Co-Assembly of Aromatic Dipeptides Into Spherical Structures That Are Similar in Morphology to Red and White Blood Cells", Journal of Materials Chemistry B, 2(17): 2583-2591, 2014.
Maity et al. "Self-Assembly of a Tripeptide into a Functional Coating that Resists Fouling", Chemical Communications, 50: 11154-11157, 2014.
Mandal et al. "The Striking Influence of SWNT-COOH on Self-Assembled Gelation", Chemical Communications, 48: 1814-1816, 2012.
Martin et al. "Exceptionally Strong Hydrogels Through Self-Assembly of an Indole-Capped Dipeptide", Chemical Communications, 50(98): 15541-15544, Published Online Oct. 30, 2014.
Orbach et al. "Self-Assembled Fmoc-Peptides as A Platform for the Formation of Nanostructures and Hydrogels", Biomacromolecules, XP055217882, 10(9): 2646-2651, Aug. 25, 2009.
Orbach et al. "The Rheological and Structural Properties of Fmoc-Peptide-Based Hydrogels: The Effect of Aromatic Molecular Architecture on Self-Assembly and Physical Characteristics", Langmuir, XP055313227, 28(4): 2015-2022, Jan. 5, 2012.
Perelshtein et al. "Sonochemical Coating of Silver Nanoparticles on Textile Fabrics (Nylon, Polyester and Cotton) and Their Antibacterial Activity", Nanotechnology, 19(24): 245705-1-245705-6, Published Online May 12, 2008.
Petkova et al. "Sonochemical Coating of Textiles With Hybrid ZnO/Chitosan Antimicrobial Nanoparticles", ACS Applied Materials & Interfaces, 6(2): 1164-1172, Published Online Jan. 3, 2014.
Reches et al. "Self-Assembly of Peptide Nanotubes and Amyloid-Like Structures by Charged-Termini-Capped Diphenylalanine Peptide Analogues", Israel Journal of Chemistry, XP009087914, 45(3): 363-371, Jun. 30, 2005.
Ryan et al. "Self-Assembly and Hydrogelation Promoted by F5-Phenylalanine", Soft Matter, 6: 475-479, 2010.
Sedman et al. "Tuning the Mechanical Properties of Self-Assembled Mixed-Peptide Tubes", Journal of Microscopy, 249(3): 165-172, Epub Jan. 11, 2013.
Shekhter Zahavi et al. "Molecular Engineering of Somatostatin Analogue With Minimal Dipeptide Motif Induces the Formation of Functional Nanoparticles", ChemNanoMat, 3(1): 27-32, Jan. 2017.
Silva et al. "Wound-Healing Evaluation of Entrapped Active Agents Into Protein Microspheres Over Cellulosic Gauzes", Biotechnology Journal, 7(11): 1375-1386, Published Online Jul. 10, 2012.
Stoyanova Petkova "Surface Nano-Structured Materials to Control Bacterial Contamination", A Thesis Submitted in Fulfilment of the Requirements for the Degree of International Doctor of Philosophy at the Universitat Politecnica de Catalunya, Barcelona, Spain, p. 1-143, 2016.
Suslick "Sonochemistry", Science, 247(4949): 1439-1445, Mar. 23, 1990.
Tao et al. "Fmoc-Modified Amino Acids and Short Peptides: Simple Bio-Inspired Building Blocks for the Fabrication of Functional Materials", Chemical Society Reviews, 45(14): 3935-3953, Jul. 11, 2016. p. 3936-3941.
Tzhayik et al. "Sonochemical Fabrication of Edible Fragrant Antimicrobial Nano Coating on Textiles and Polypropylene Cups", Ultrasonics Sonochemistry, 38: 614-621, Available Online Aug. 16, 2016.

(56) References Cited

OTHER PUBLICATIONS

Van Loveren "Antimicrobial Activity of Fluoride and Its in vivo Importance: Identification of Research Questions", Caries Research, 35, Supplemental 1: 65-70, 2001.
Wang et al. "High-Water-Content Mouldable Hydrogels by Mixing Clay and a Dendritic Molecular Binder", Nature, 463 (7279): 339-43, 2010.
Yuran et al. "Coassembly of Aromatic Dipeptides Into Biomolecular Necklaces", ACS Nano, 6(11): 9559-9566, Epub Oct. 19, 2012.
Final Official Action Dated Oct. 28, 2021 from US Patent and Trademark Office Re. U.S. Appl. No. 16/942,837. (10 pages).
Official Action Dated Apr. 16, 2021 from the US Patent and Trademark Office Re. U.S. Appl. No. 16/942,837. (14 pages).
Schnaider at al. "Self-Assembling Dipeptide Antibacterial Nanostructures with Membrane Disrupting Activity"; Nature Communications, 8:1365: 1-10, 2017.
Yan et al. "Self-Assembly and Application of Diphenylalanine-Based Nanostructures"; Chemical Society Reviews, 39: 1877-1890, 2010.

\* cited by examiner

Fmoc-F$_5$-Phe FmocFF

Fmoc-F$_5$-Phe 3:1 1:1 1:3 Fmoc-FF 1:1 Fmoc-F$_5$-Phe

SELF-ASSEMBLED HYBRID HYDROGELS FORMED OF A SHORT AROMATIC PEPTIDE AND AN AROMATIC AMINO ACID

RELATED APPLICATIONS

This application is a National Phase of PCT Patent Application No. PCT/IL2018/050773 having International filing date of Jul. 13, 2018, which claims the benefit of priority under 35 USC § 119(e) of U.S. Provisional Patent Application No. 62/531,905 filed on Jul. 13, 2017. The contents of the above applications are all incorporated by reference as if fully set forth herein in their entirety.

FIELD AND BACKGROUND OF THE INVENTION

The present invention, in some embodiments thereof, relates to materials and, more particularly, but not exclusively, to self-assembled hybrid hydrogels formed of two or more types of short peptides/amino acids, which exhibit improved mechanical properties, and to uses thereof.

Molecular self-assembly serves as a key approach for the formation of biocompatible peptide-based hydrogels. Specifically, low molecular weight hydrogelators have been widely explored in recent years, particularly for biotechnological and medical applications, due to their ability to act as building blocks for three-dimensional (3D) hydrogel structures formation, which mimic the extracellular matrix (ECM) [Fleming, S. & Ulijn, R. V. Chem. Soc. Rev. 43, 8150-8177, (2014); Fichman, G. & Gazit, Acta Biomater. 10, 1671-1682, (2014)]. These self-assembled hydrogels have been found to form a support scaffold for the growth of cells and are being used in the field of regenerative medicine [Ellis-Behnke, R. G. et al. Proc. Nat. Acad. Sci. U.S.A. 103, 5054-5059, (2006)]. The self-assembled ultra-short peptide building blocks are easy to fabricate and can be simply chemically and biologically decorated [Mahler et al. Adv. Mater. 18, 1365-1370, (2006); Jayawarna, V. et al. Adv. Mater. 18, 611-614, (2006)].

Recently, it has been shown that peptide-based hydrogel could be printed in order to support human stem cells differentiation [Loo, Y. et al. Nano Letters 15, 6919-6925, (2015)] and functional motifs could be linked to self-assembled peptide to allow such differentiation and proliferation [Gelain, F. et al. ACS Nano 5, 1845-1859, (2011)].

WO 2004/052773 and WO 2004/060791 disclose self-assembled peptide tubular nanostructures made of short aromatic peptides, and uses thereof.

WO 2007/0403048 and Reches and Gazit [Isr. J. Chem. 2005; 45: 363-371] disclose the assembly of tubular and fibrillar (amyloid-like) structures by non-charged, end-capping modified aromatic peptides.

Adler-Abramovich et al. [J. Pept. Sci. 2008; 14: 217-223] describe that two types of nanostructures—nanotubes and nanospheres, are obtained by the self-assembly of the aromatic dipeptide Phe-Phe, while using different end-capping moieties.

Ample studies have focused on Fmoc-modified oligopeptides and their ability to form hydrogels. See, for example, Burch, R. M. et al. Proc. Nat. Acad. Sci. U.S.A. 88, 355-359, (1991).

An example of Fmoc-based hydrogels is the Fmoc-FF peptide that efficiently assembles into fibrous hydrogels under physiological conditions [Jayawarna, V. et al. Adv. Mater. 18, 611-614, (2006); Mahler et al., 2006, supra; and WO 2007/043048]. The properties of the fibrous hydrogels have been characterized and used for various applications [Adler-Abramovich, L. & Gazit, E. Chem. Soc. Rev. 43, 6881-6893, (2014)].

The single amino acid phenylalanine was shown to form ordered structures [Adler-Abramovich, L. et al. Nat. Chem. Biol. 8, 701-706, (2012)], and Fmoc-modified aromatic single amino acids analogues, Fmoc-Phe and Fmoc-Tyr were also shown to form ordered fibrillar assemblies [Draper, E. R. et al. Cryst Eng Comm 17, 8047-8057, (2015)].

Fmoc-modified aromatic non-coded single amino acids have also been investigated as hydrogelators. See, for example, Fichman et al. Cryst Eng Comm 17, 8105-8112, (2015); Orbach, R. et al. Biomacromolecules 10, 2646-2651, (2009); and Ryan et al. Soft Matter 6, 3220-3231, (2010).

The fluorinated peptide derivative of Fmoc-Phe, Fmoc-pentafluorophenylalanine (Fmoc-F5-Phe), has also been reported to rapidly self-assemble into ordered structures [Ryan et al. Soft Matter 6, 3220-3231, (2010)].

In spite of their advantages, the physical properties of short peptide-based and amino acid-based hydrogels are limited due to the chemical nature of the chosen building blocks, making the modulation of the physical properties highly challenging in each case.

Co-assembly of two building blocks into one ordered structure has been shown to provide a new material exhibiting enhanced properties.

It has been shown that the co-assembly of short peptide building blocks can produce complex architectures such as "beads on a string", hydrogels and tubes. See, for example, Orbach et al. Langmuir 2012, 28, 2015-2022; Carny et al. Nano Lett. 2006, 6, 1594-7.

Sedman et al. [J. of Microscopy, 2013, pp. 1-8] teach nano- and micro-scale fibrillar and tubular structures formed by mixing two aromatic dipeptides, Phe-Phe and D-Nal-Nal, and describe that the mechanical properties of the structures depend on the percentage of each peptide in the mixture.

Yuran et al. [ACS Nano, 2012, 6 (11), pp 9559-9566] describe the formation of complex peptide-based structures by the co-assembly of Phe-Phe-OH and Boc-Phe-Phe-OH, into a construction of beaded strings, where spherical assemblies are connected by elongated elements.

Malty et al. [J. Mater. Chem. B, 2014, 2, 2583-2591] describe the co-assembly of two aromatic dipeptides, diphenylalanine and Fmoc-L-DOPA(acetonated)-D-Phe-OMe, into different spherical structures that are similar in morphology to either red or white blood cells.

U.S. Patent Application Publication No. 2016-0326215 describes self-assembled hybrid materials formed of two types of aromatic dipeptides, which differ from one another by the type and/or presence of their end-capping moiety.

Synthetic triskelion peptide, which self-assembles into spherical structures, was co-assembled with diphenylalanine fibrils [Ghosh, S. & Verma, S. Chem. Eur. J. 14, 1415-1419, (2008)].

Co-assembly of Fmoc-F5-Phe with PEG-functionalized monomers was described [Ryan, D. M., Anderson, S. B. & Nilsson, B. L. Soft Matter 6, 3220-3231, (2010)].

Co-assembly of Fmoc-FF and Fmoc-FG was also described [Orbach, R. et al. Langmuir 28, 2015-2022, (2012)].

Additional background art includes Mandal et al., Chem. Commun. 48, 1814-1816, (2012); Li, J. et al. J. Am. Chem. Soc. 135, 542-545, (2013); Wang et al. Nature 463, 339-343, (2010); Jayawarna, et al. Acta Biomater. 5, 934-943, (2009); Cheng et al. Langmuir 26, 4990-4998, (2010); Dudukovic, N. A. & Zukoski, C. F. Langmuir 30, 4493-4500, (2014);

Van Loveren, C. *Caries Res.* 35, 65-70, (2001); Malty et al. *Chem. Commun.* 50, 11154-11157, (2014); Martin et al. *Chem. Commun.* 50, 15541-15544, (2014); Shekhter-Zahavi, T. et al. *Chem Nano Mat* 3, 27, (2017); Sedman et al., *J Microsc.* 2013 March; 249(3): 165-172; Adler-Abramovich, L. et al. *ACS Nano*, (2016); and Halperin-Sternfeld et al., *Chem. Commun.*, 2017, 53, 9586-9589.

SUMMARY OF THE INVENTION

According to an aspect of some embodiments of the present invention there is provided a hybrid hydrogel comprising a three-dimensional network of fibrillar nanostructures, at least a portion of the fibrillar nanostructures being formed of a plurality of aromatic moieties, the plurality of aromatic moieties comprising at least two different types of aromatic moieties, at least one type of the aromatic moieties being an end-capping modified aromatic dipeptide and at least one type of the aromatic moieties being an amine-modified halogenated aromatic amino acid.

According to some of any of the embodiments described herein, an average length of the fibrillar nanostructures formed of the plurality of aromatic moieties is lower than 10 microns, or lower than 8 microns, or lower than 6 microns, or lower than 5 microns.

According to some of any of the embodiments described herein, the hybrid hydrogel is characterized by a storage modulus, G', higher by at least 2-folds, or at least 3-folds, or at least 5-folds, of a storage modulus of a hydrogel made of the end-capping modified aromatic dipeptide.

According to some of any of the embodiments described herein, the hybrid hydrogel is characterized by a storage modulus, G', of at least 20,000, or at least 50,000, or at least 100,000, or at least 150,000 Pa.

According to some of any of the embodiments described herein, a molar ratio of the at least two types of aromatic moieties in the plurality of aromatic moieties determines a storage modulus, G', of the hydrogel and/or an average length of the fibrillar nanostructures formed of the plurality of aromatic moieties.

According to some of any of the embodiments described herein, each of the fibrillar nanostructures is formed of the plurality of aromatic moieties.

According to some of any of the embodiments described herein, a molar ratio of the end capping-modified aromatic dipeptide and the amine-modified aromatic amino acid ranges from 1:10 to 10:1, or from 1:5 to 5:1 or from 3:1 to 1:3, or is 1:1.

According to some of any of the embodiments described herein, the end-capping modified aromatic dipeptide is an end-capping modified homodipeptide.

According to some of any of the embodiments described herein, the end-capping modified homodipeptide is an end-capping modified diphenylalanine.

According to some of any of the embodiments described herein, the end-capping modified dipeptide is an N-terminus modified dipeptide.

According to some of any of the embodiments described herein, the end-capping modified aromatic dipeptide comprises an aromatic end capping moiety.

According to some of any of the embodiments described herein, the aromatic end capping moiety is Fmoc.

According to some of any of the embodiments described herein, the halogenated aromatic amino acid comprises in its side chain an aromatic moiety substituted by 1, 2, 3, 4, 5 or more halogen substituents.

According to some of any of the embodiments described herein, the halogenated aromatic amino acid is a fluorinated aromatic amino acid.

According to some of any of the embodiments described herein, the halogenated aromatic amino acid is a halogenated phenylalanine.

According to some of any of the embodiments described herein, the halogenated aromatic amino acid is F5-phenylalanine.

According to some of any of the embodiments described herein, the amine-modified aromatic amino acid comprises an aromatic moiety attached to the alpha amine of the amino acid.

According to some of any of the embodiments described herein, the aromatic moiety is Fmoc.

According to an aspect of some embodiments of the present invention there is provided a hybrid hydrogel essentially as described herein.

According to an aspect of some embodiments of the present invention there is provided a process of preparing the hydrogel hybrid as described in any of the respective embodiments and any combination thereof, the process comprising contacting a first solution comprising the end-capping modified aromatic dipeptide and a first organic solvent, at least a second solution comprising the amine-modified halogenated aromatic amino acid and a second organic solvent, and an aqueous solution, thereby preparing the hybrid hydrogel.

According to an aspect of some embodiments of the present invention there is provided a process of preparing the hybrid hydrogel, essentially as described herein.

According to an aspect of some embodiments of the present invention there is provided an article-of-manufacturing, comprising the hybrid hydrogel as described herein in any of the respective embodiments.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
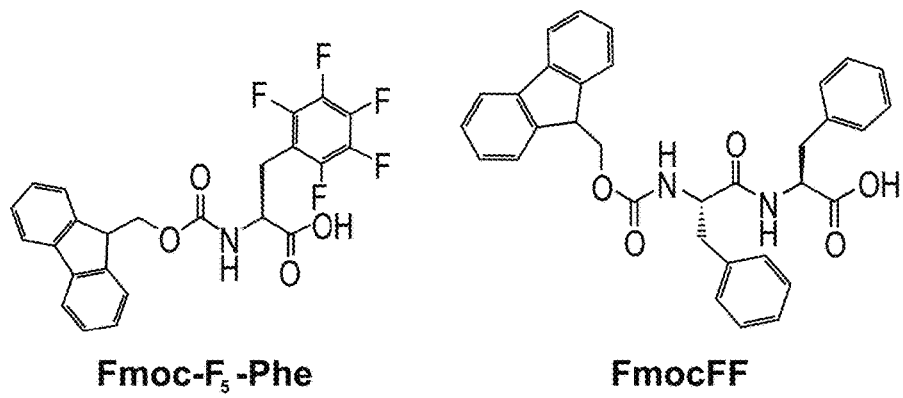
Figure 1B:
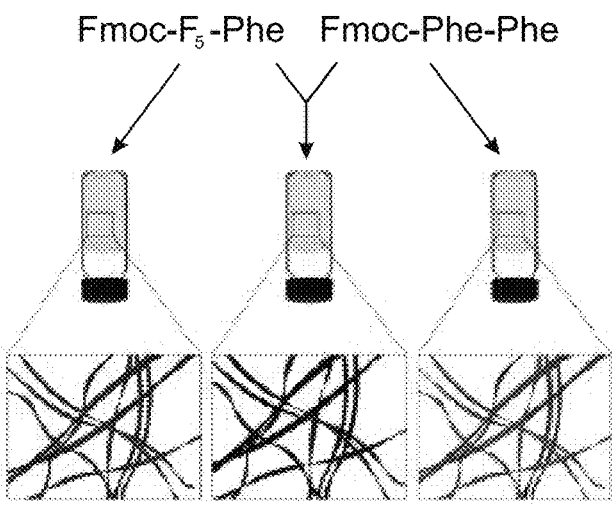
Figures 1C, 1D:
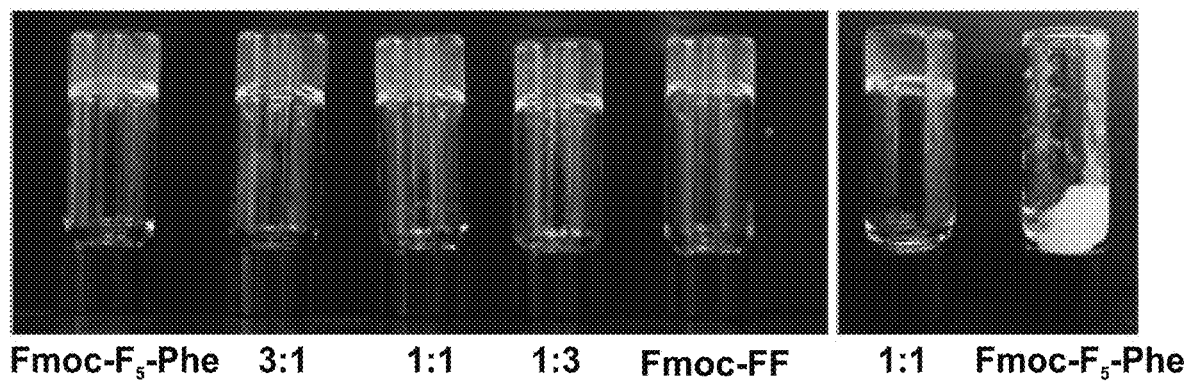

FIGS. 1A-D present the molecular structures of the exemplary building blocks Fmoc-FF and Fmoc-F5-Phe (FIG. 1A); a schematic presentation of gelation process of each of the exemplary building block separately and the formation of exemplary hybrid hydrogel (FIG. 1B); Inverted tubes of (left to right) Fmoc-F5-Phe, Fmoc-F5-Phe/Fmoc-FF 3:1, 1:1, 1:3 respectively and Fmoc-FF (FIG. 1C); and inverted tubes of Fmoc-F5-Phe (right) and 1:1 hybrid hydrogel (left) three week after preparation (FIG. 1D).

Figure 2:
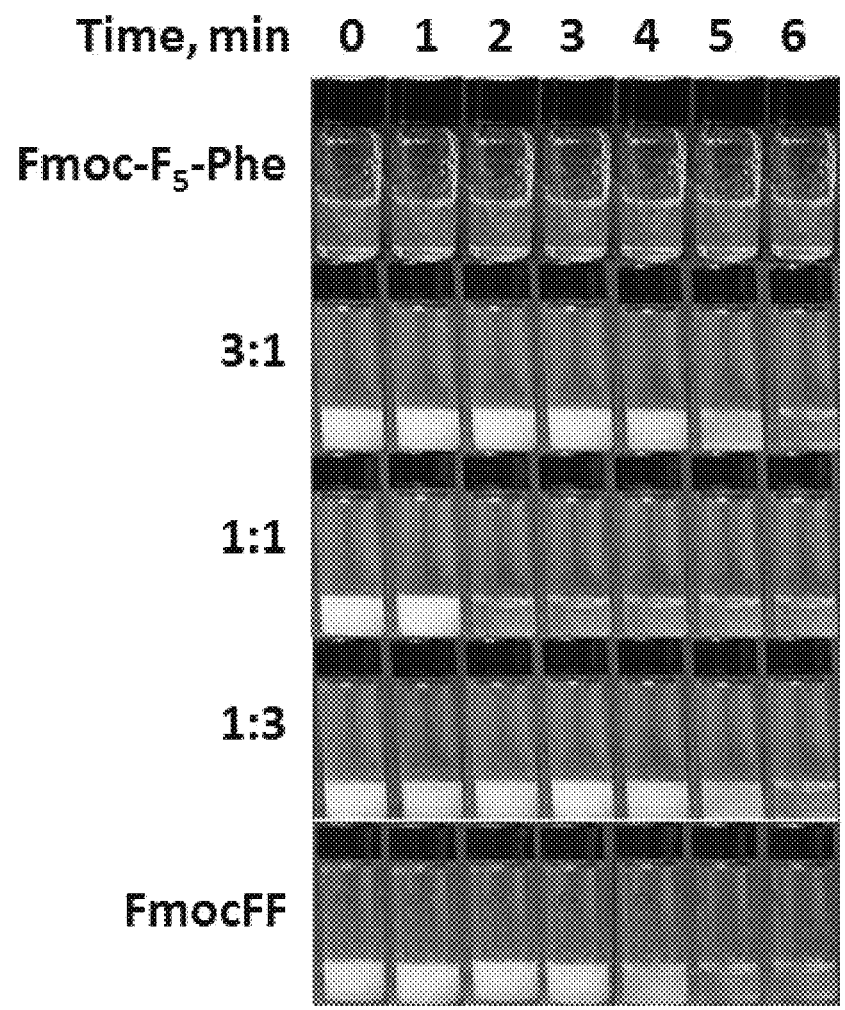

FIG. 2 presents images showing the gelation kinetics of the formed exemplary hydrogels taken at 1-minute intervals, showing the transition from a cloudy mixture to a transparent hydrogel within minutes.

Figure 3A:
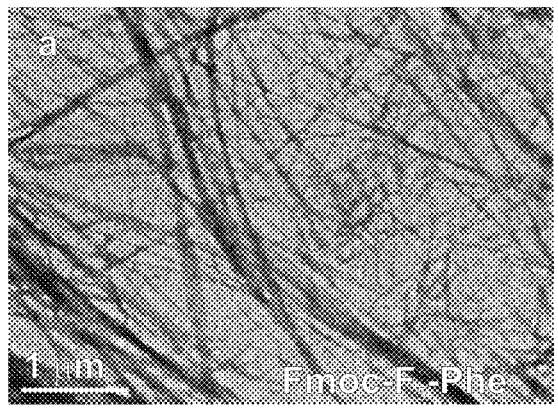
Figure 3B:
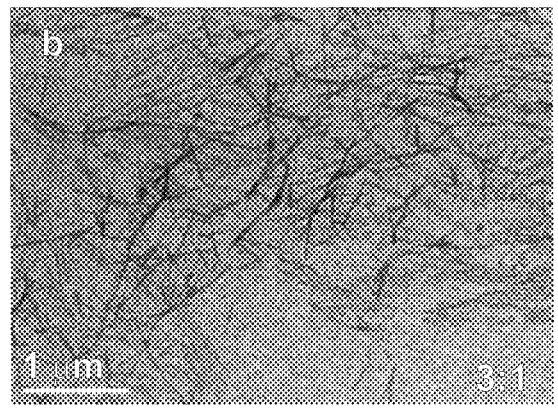
Figure 3C:
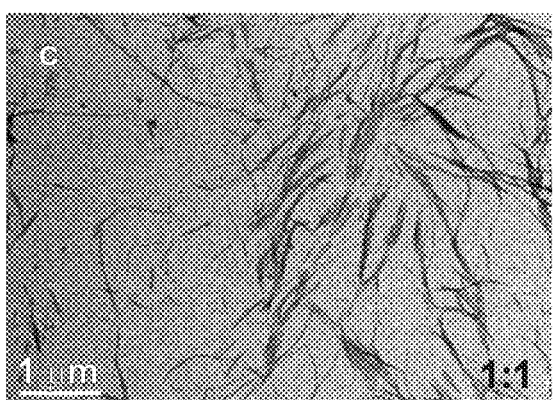
Figure 3D:
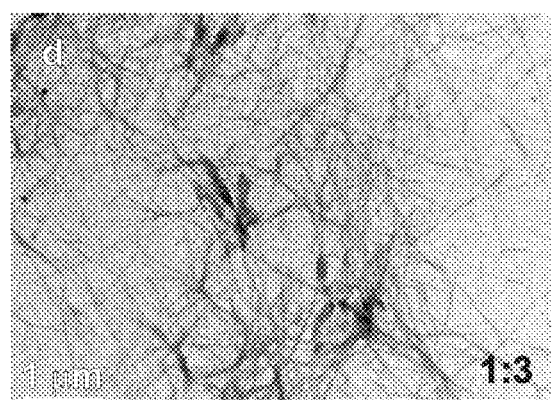
Figure 3E:
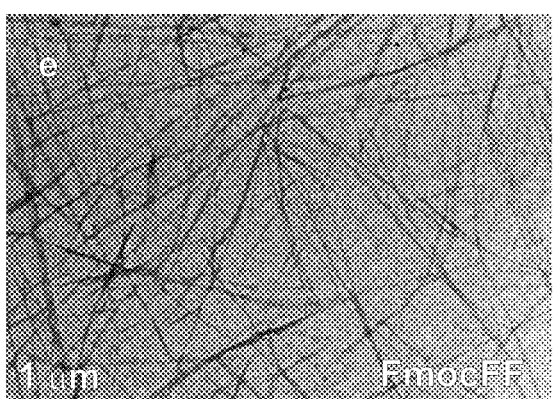
Figure 3F:
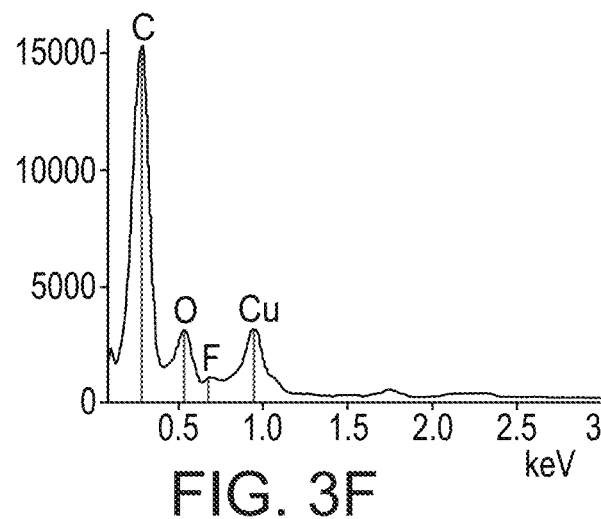

FIGS. 3A-F present the TEM structural analyses of Fmoc-F5-Phe-OH (FIG. 3A); of the exemplary hybrid hydrogels 3:1, 1:1 and 1:3, (FIGS. 3B, 3C and 3D, respectively); and of Fmoc-FF (FIG. 3E), and energy-dispersive X-ray spectroscopy (EDS) analysis of the exemplary 3:1 hybrid hydrogel showing the fluoride peak (FIG. 3F).

Figure 4A:
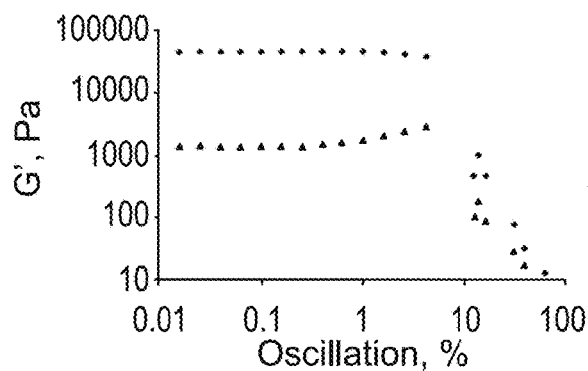
Figure 4B:
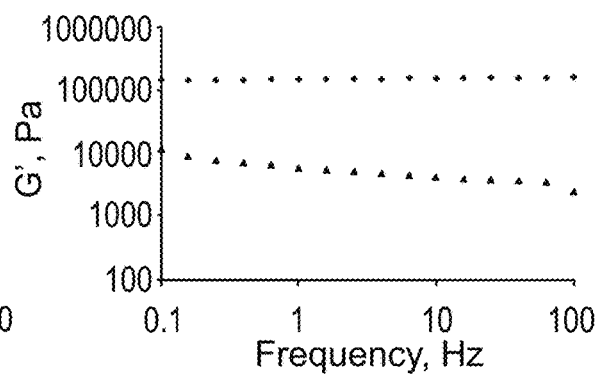
Figure 4C:
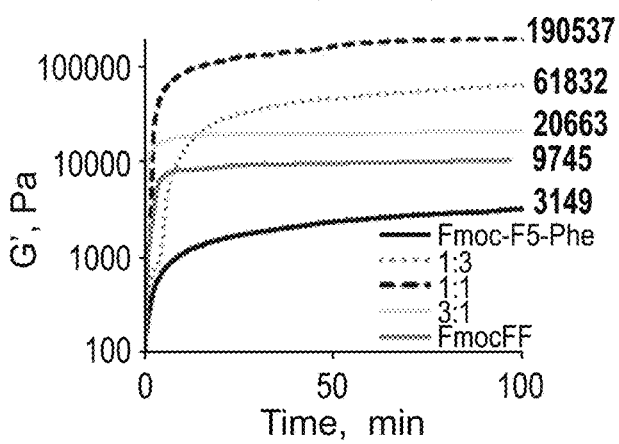
Figure 4D:
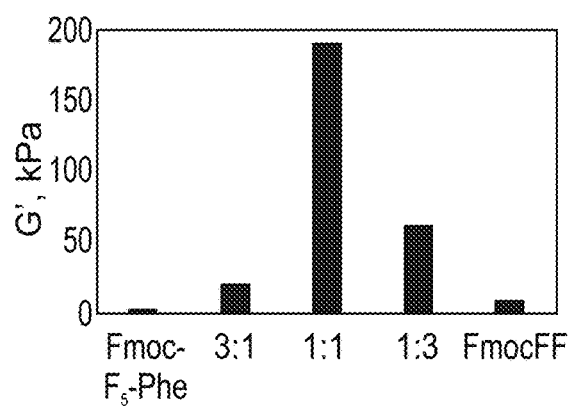
Figure 4E:
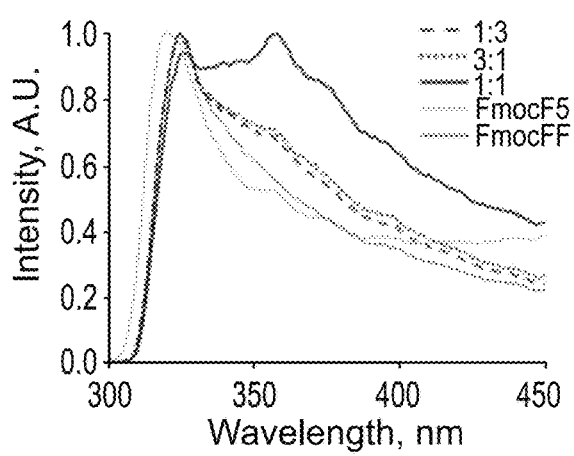
Figure 4F:
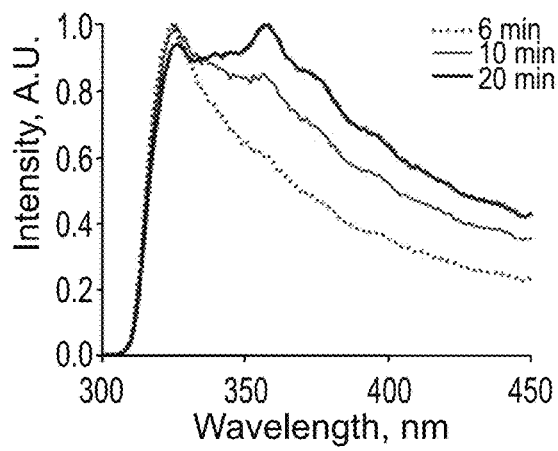

FIGS. 4A-F data obtained in rheological analysis of different hydrogels at 25° C.: Strain Sweep (FIG. 4A) and Frequency Sweep (FIG. 4B) oscillatory measurements of the exemplary 1:1 hybrid hydrogel; in situ time sweep oscillation measurements of hydrogels formation (FIG. 4C); The dependence of mechanical properties of gels on different types of exemplary hybrids (FIG. 4D); UV-vis spectra of different exemplary hydrogels taken 20 minutes after gel preparation (FIG. 4E); and UV-vis spectra of an exemplary 1:1 hybrid hydrogel during gel formation 6, 10 and 20 minutes after gel preparation (FIG. 4F).

Figure 5:
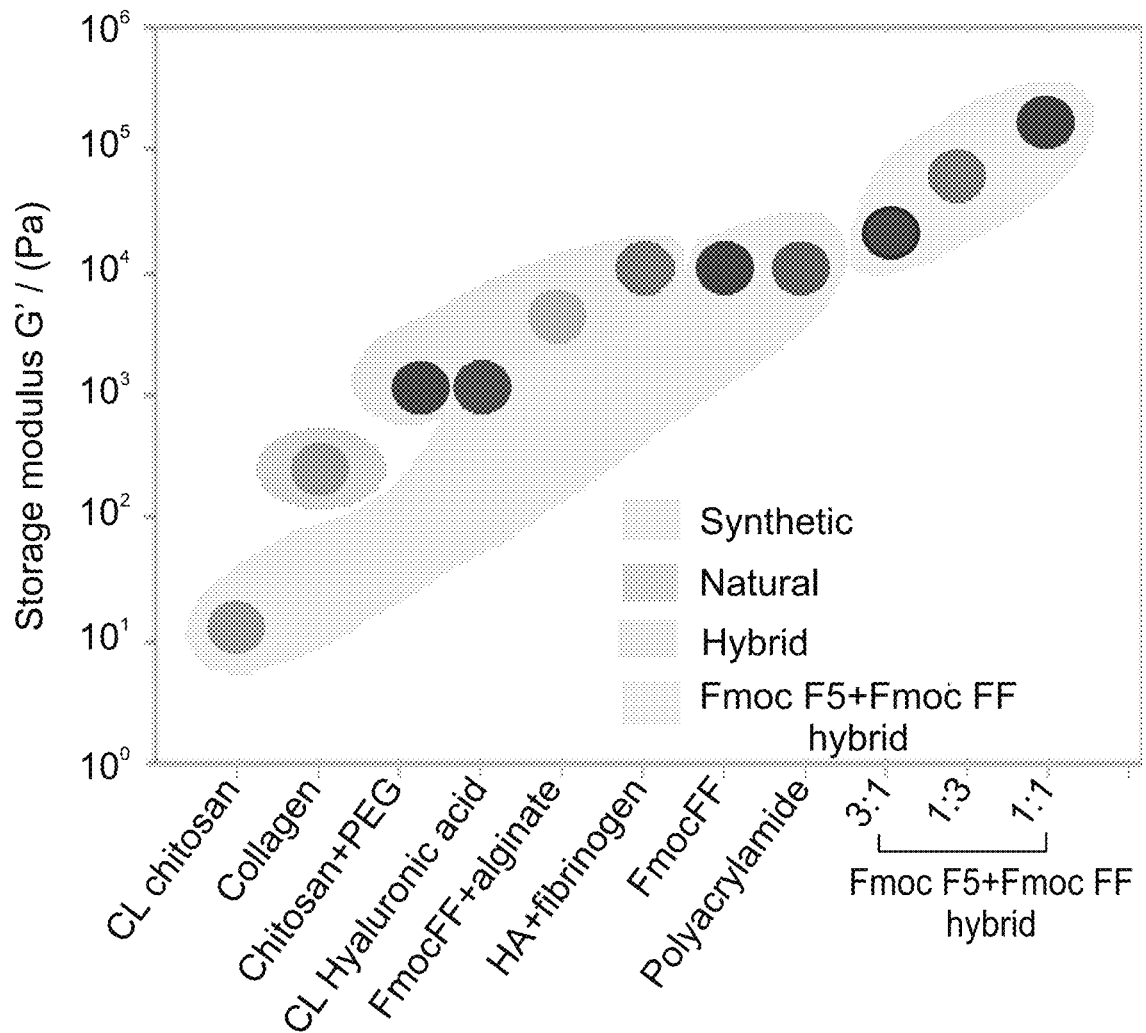

FIG. 5 presents comparative plots showing the storage modulus (G') of the hybrid Fmoc-F5-Phe/Fmoc-FF hydrogels according to some embodiments of the present invention (blue region); and of hydrogels previously reported in the art, including the synthetic hydrogels (green region) chitosan crosslinked with glutaraldehyde [W. Argüelles-Monal et al, *Biomaterials Science,* 2014, 2, 1661-1671]' Fmoc-FF and polyacrylamide gels [Y.-h. Lee et al., *Integrative Biology,* 2013, 5, 1447-1455]; of the natural hydrogel (orange region) collagen [M. Sawkins et al., *Acta biomaterialia,* 2013, 9, 7865-7873]; and of the hybrid gels (yellow region) of chitosan and PEG [B. Yang et al, *Polymer Chemistry,* 2012, 3, 3235-3238], Fmoc-FF and alginate [X. Gong et al., *Materials science & engineering. C, Materials for biological applications,* 2016, 58, 478-486], and hyaluronic acid and fibrinogen [Y. Ma et al., *Biomaterials Science,* 2014, 2, 1661-1671].

Figure 6:
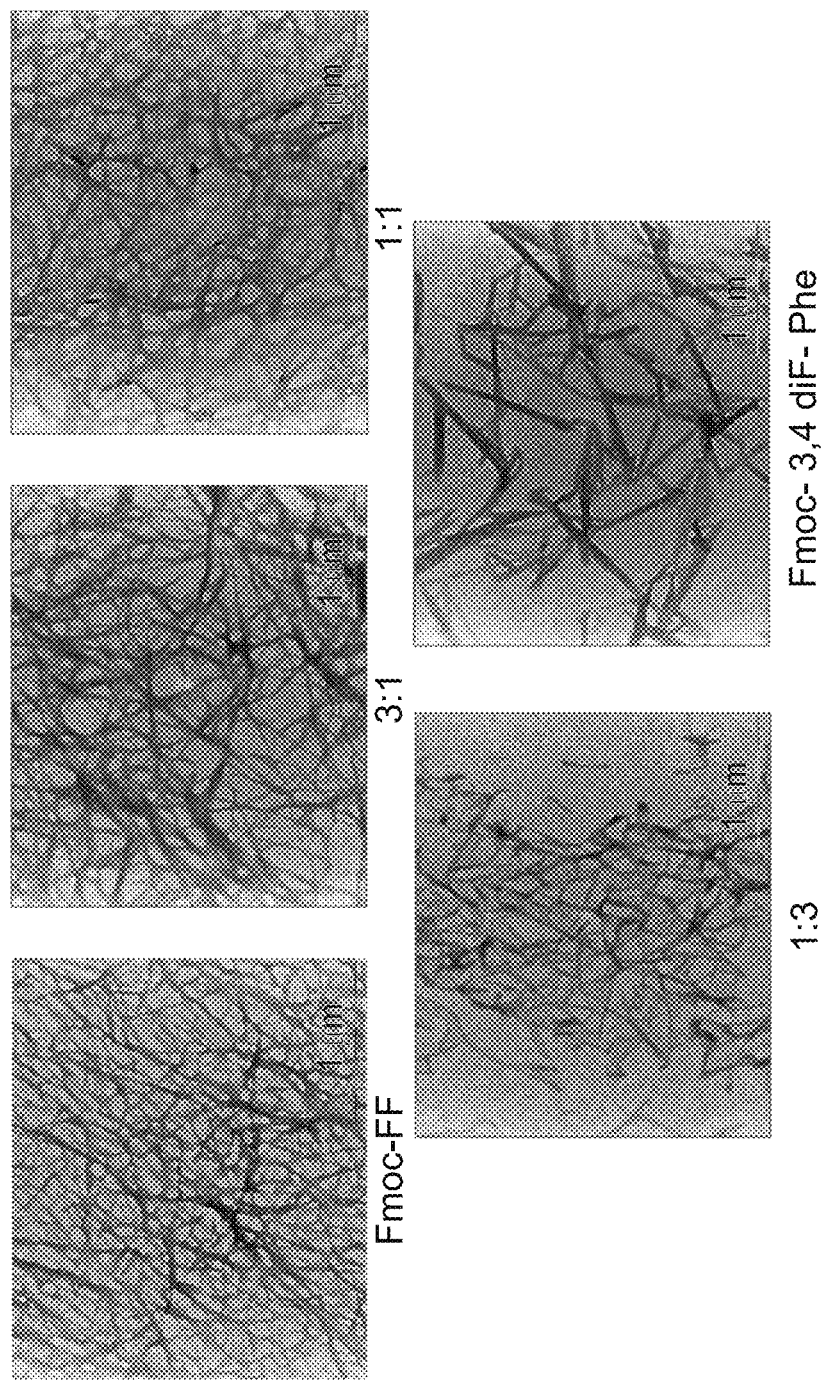

FIG. 6 presents the TEM structural analyses of hydrogels formed of Fmoc-3,4-diF-Phe-OH, or Fmoc-FF, and of the exemplary hybrid hydrogels thereof at a molar ratio of 3:1, 1:1 and 1:3.

Figure 7:
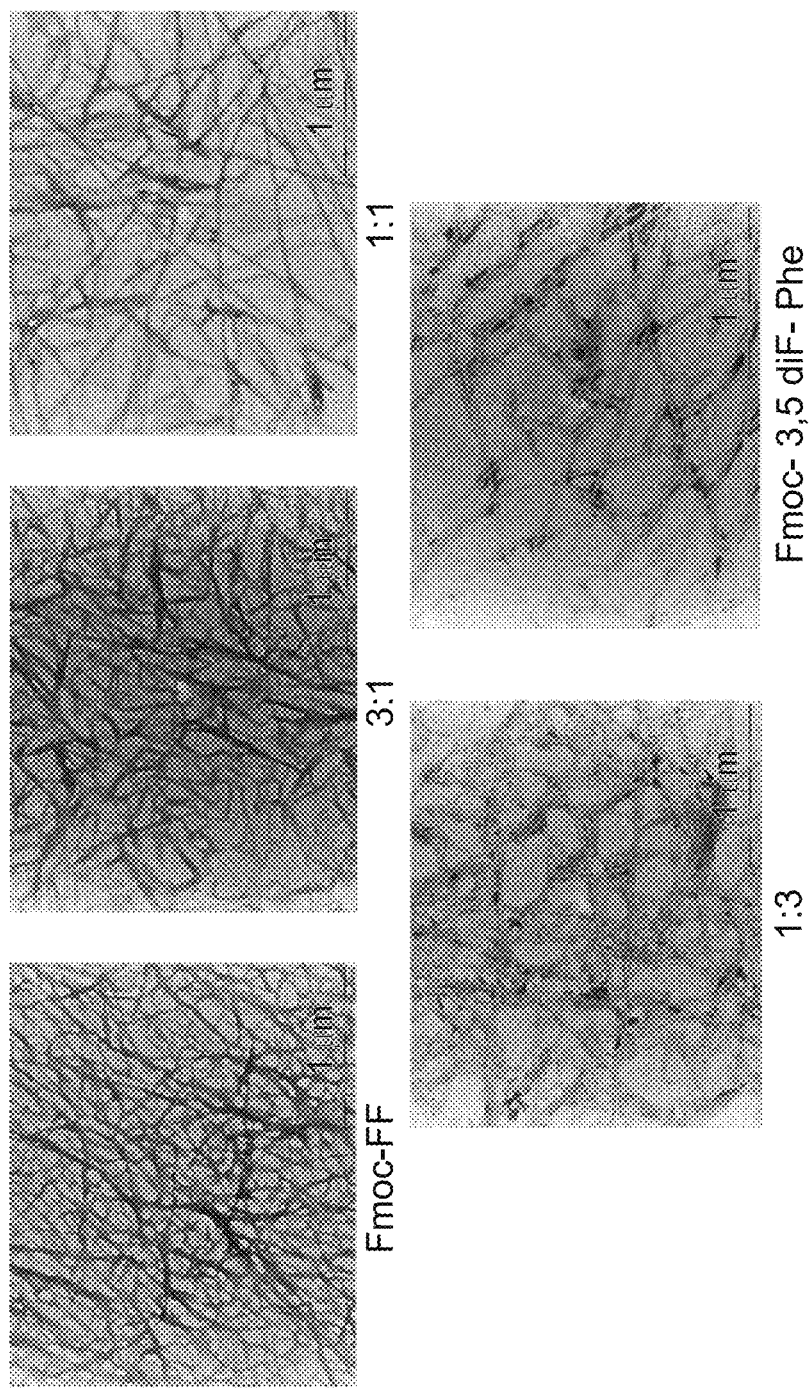

FIG. 7 presents the TEM structural analyses of hydrogels formed of Fmoc-3,5-diF-Phe-OH, or Fmoc-FF, and of the exemplary hybrid hydrogels thereof at a molar ratio of 3:1, 1:1 and 1:3.

Figure 8:
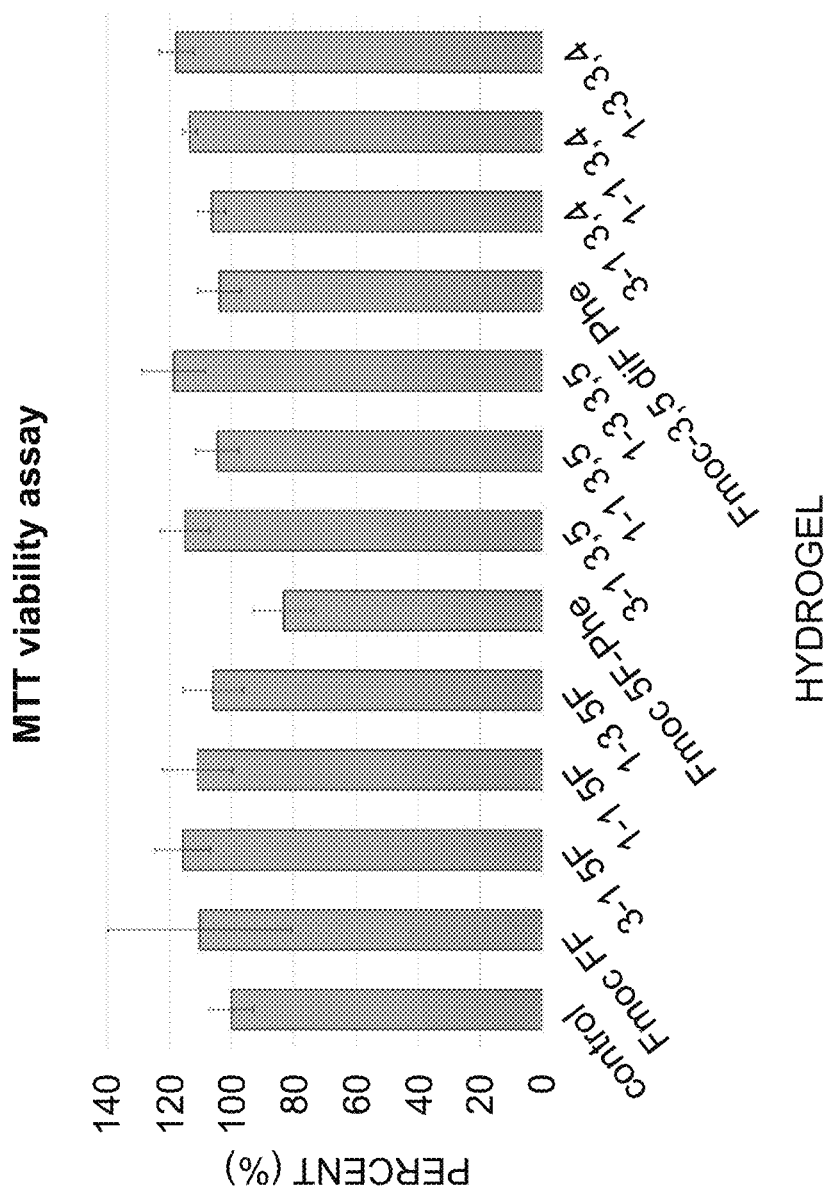

FIG. 8 is a bar graph showing the data obtained in an MTT-based cell growth test, as described in Example 4 hereinunder, in the presence of various exemplary hybrid hydrogels according to the present embodiments.

DESCRIPTION OF SPECIFIC EMBODIMENTS OF THE INVENTION

The present invention, in some embodiments thereof, relates to materials and, more particularly, but not exclusively, to self-assembled hybrid hydrogels formed of two or more types of short peptides/amino acids, which exhibit improved mechanical properties, and to uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, molecular self-assembly is a key direction in current nanotechnology. Yet, the physical properties of formed assemblies are directed by the inherent characteristics of the building blocks used. In contrast, molecular co-assembly, at varied stoichiometric ratios, substantially increases the structural and functional diversity, thus allowing tuning of both the architecture as well as the physical properties of ordered assemblies.

As further discussed hereinabove, extensive studies have been performed in the context of molecular self-assembly by utilizing hydrogels based on short peptides or single amino acids building blocks. However, an inherent limitation in the utilization of these hydrogels is that their physical properties are determined by the chemical nature of the chosen building block in each case.

To overcome this limitation and to significantly increase the chemical and functional diversity of such hydrogels, co-assembly of several building blocks into a single hydrogel has been explored as a strategy towards obtaining novel physical properties. This concept is naturally occurring in biological systems, such as the extracellular matrix, where the physical properties of the scaffold are modulated by combining several basic building blocks, including proteins and polysaccharides.

The fluorinated peptide derivatives of Fmoc-Phe, including the Fmoc-pentafluorophenylalanine (Fmoc-$F_5$-Phe-OH), have been studied, as described hereinabove. The Fmoc-$F_5$-Phe-OH hydrogel has shown to feature a low stability over time.

The present inventors have conceived using the co-assembly approach to generate hydrogels combining the advantages of halogenated (e.g., fluorinated) molecular scaffold along with superior mechanical properties and durability.

While reducing the present invention to practice, the present inventors have applied the co-assembly approach using various halogenated Fmoc-phenylalanine (e.g., Fmoc-pentafluoro-phenylalanine; Fmoc-F5-Phe) and Fmoc-diphenylalanine (Fmoc-FF).

While co-assembly of two building blocks into one ordered structure can form a new material with an entirely new set of properties or enhanced properties of the pure materials assembled from those building blocks, the present inventors have uncovered that the addition of Fmoc-FF to Fmoc-F5-Phe-OH during self-assembly significantly increased the stability of the resulting hybrid hydrogel and decreased the time of gelation. Moreover, the present inventors surprisingly uncovered that by co-assembling these two molecules the mechanical properties (strength and rigidity) of the resulting hybrid hydrogel were significantly enhanced in comparison to gels prepared from both materials separately, and extremely strong rigid hydrogels, featuring a synergistic rather than linear effect.

Thus, the present inventors have applied for a synergistic modulation of the mechanical properties of peptide hydrogels. This results in a much higher stiffness than that achieved by the use of each of the building blocks exclusively or their linear combination. This synergistic improvement results in a hybrid-hydrogel with extraordinary G' values of up to 190,000 Pa. The various hybrid-hydrogel formation kinetics, its durability, and fibrils composition, were further characterized. This approach provides a conceptual framework for the utilization of co-assembly strategy to go beyond the physical properties obtained by self-assembly.

As shown in the Examples section that follows, the formation of a long-term stable hybrid hydrogel formed by two building blocks, Fmoc-FF and Fmoc-F5-Phe, with functional fluoride decoration, has been demonstrated. This is the first demonstration of the synergistic effect on the mechanical properties through using a molecular co-assemblies approach.

The formation of hybrid hydrogels by co-assembly of Fmoc-FF and Fmoc-F5-Phe and the stability thereof over time are presented in FIGS. 1A-D and 2, and TEM images of the formed structures are presented in FIGS. 3A-F.

The remarkable mechanical properties of the formed hybrid hydrogels are presented in FIGS. 4A-D and 5. Thus, the 1:1 hybrid hydrogel was shown to exhibit remarkable mechanical properties with a storage modulus as high as 190 kPa, an order of magnitude higher than hydrogels formed by each of the individual building blocks, and much higher than other hydrogels.

The formation of hybrid hydrogels made of Fmoc-FF and other halogenated Fmoc-Phe has also been demonstrated, as shown in FIGS. 6 and 7.

All of the formed hybrid hydrogels were demonstrated as biocompatible, as shown in FIG. 8, indicating their suitability for use in various medical applications.

Thus, supramolecular co-assembly approach is shown herein to result in ultra-rigid biocompatible hydrogels with controllable mechanical properties that can be utilized for tissue engineering and other biotechnological applications, and provides a conceptual framework for the significant expansion of nanotechnology to fully exploit the prospects of multi-component supramolecular chemistry.

The hybrid hydrogels disclosed herein can be advantageously used in many fields and applications of tissue engineering.

The hybrid hydrogels disclosed herein can be utilized in, for example, orthopedic devices, degenerative discs, and in the treatment of cartilaginous defects, wounds and skin healing, ulcers of diabetics, gape for hernia, nerve elongation, and bridging central and peripheral nervous system region losses.

According to an aspect of some embodiments of the present invention there is provided a hybrid hydrogel comprising a three-dimensional network of fibrillar nanostructures.

As used herein and is well-known in the art, the term "hydrogel" refers to a gel, typically semi-solid, material that comprises 3D fibrous networks formed of natural or synthetic chains, typically containing more than 80%, or more than 90% or more than 95% or more than 99%, by weight or by volume, water or an aqueous solution.

As used herein the phrase "fibrous network" refers to a set of connections formed between a plurality of fibrous components. Herein, the fibrous components are composed of a plurality of fibrillar nanostructures, at least a portion of which, or each, being formed upon self-assembly of aromatic building blocks (a plurality of aromatic moieties).

According to embodiments of the present invention, the three-dimensional fibrous network comprises fibrillar nanostructures formed of a plurality of aromatic moieties.

As used herein a "hybrid hydrogel" is a hydrogel as defined herein, in which the fibrous network in formed of more than one material.

The hybrid hydrogel can be such that two or more types of fibrous components form the 3D fibrous network, and each type of a fibrous component is formed of the same material, such that, for example, one type of aromatic moieties form one type of fibrillar nanostructures and another type of aromatic moieties form another type of fibrillar nanostructures, and the fibrous network is formed of fibrous components composed of these two types of fibrillar nanostructures.

The hybrid hydrogel can alternatively or in addition be such that at least a portion of the fibrous components are fibrillar nanostructures, each formed of two or more types of aromatic moieties, that is, each is formed of two or more materials.

As used herein the phrase "fibrillar nanostructure" refers to a filament or fiber having a diameter or a cross-section of less than 1 μm (preferably less than about 100 nm, more preferably less than about 50 nm, and even more preferably less than about 10 nm). The length of the fibrillar nanostructure of the present invention is preferably at least 10 nm, more preferably at least 100 nm and even more preferably at least 500 nm. Preferably, the fibrillar nanostructures described herein are characterized as non-hollowed or at least as having a very fine hollow.

According to some embodiments of the present invention, the fibrillar nanostructures formed of the plurality of aromatic moieties as described herein have an average diameter or a cross-section of less than 1 μm, or an average diameter that ranges from about 1 nm to about 500 nm, more preferably from about 10 nm to about 500 nm, more preferably from about 10 nm to about 200 nm and more preferably from about 10 nm to about 100 nm.

According to some of any of the embodiments described herein, an average length of the fibrillar nanostructures formed of the plurality of aromatic moieties as described herein is lower than 10 microns, or lower than 8 microns, or lower than 6 microns, or lower than 5 microns.

The phrase "aromatic moiety" as used herein describes a synthetic or naturally-occurring compound that comprises one or more aromatic groups.

As used herein, the phrase "aromatic group" describes a monocyclic or polycyclic moiety having a completely conjugated pi-electron system. The aromatic group can be an all-carbon moiety or can include one or more heteroatoms such as, for example, nitrogen, sulfur or oxygen. The aromatic group can be substituted or unsubstituted, whereby when substituted, the substituent can be, for example, one or more of alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine.

Exemplary aromatic groups include, for example, phenyl, biphenyl, naphthalenyl, phenanthrenyl, anthracenyl, [1,10] phenanthrolinyl, indoles, thiophenes, thiazoles and, [2,2'] bipyridinyl, each being optionally substituted. Thus, representative examples of aromatic groups that can serve as the side chain within the aromatic amino acid described herein include, without limitation, substituted or unsubstituted naphthalenyl, substituted or unsubstituted phenanthrenyl, substituted or unsubstituted anthracenyl, substituted or unsubstituted [1,10]phenanthrolinyl, substituted or unsubstituted [2,2']bipyridinyl, substituted or unsubstituted biphenyl and substituted or unsubstituted phenyl. The aromatic group can alternatively be substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine.

According to embodiments of the present invention, an aromatic moiety is or comprises an aromatic amino acid.

The phrase "aromatic amino acid", as used herein, refers to an amino acid residue that comprises an aromatic group as defined herein in its side-chain, for example, a substituted or unsubstituted naphthalenyl and/or a substituted or unsubstituted phenyl. The aromatic moiety can alternatively be a substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine.

When substituted, the phenyl, naphthalenyl or any other aromatic moiety includes one or more substituents such as, but not limited to, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

Exemplary substituted phenyls may be, for example, pentafluoro phenyl, iodophenyl, biphenyl and nitrophenyl.

According to embodiments of the present invention, the plurality of aromatic moieties forming the fibrillar nanostructures in the hydrogel comprise at least two types of aromatic moieties, one type being an aromatic amino acid as described herein, and one type being an aromatic dipeptide.

According to embodiments of the present invention the fibrillar nanostructures in the hydrogel are formed of a plurality of aromatic amino acids as described herein and a plurality of aromatic dipeptides as described herein.

The phrase "aromatic dipeptide" describes a peptide composed of two amino acid residues, at least one, and preferably both, being an aromatic amino acid as defined herein.

According to some of any of the embodiments described herein, the aromatic dipeptide comprises in its side chain an aromatic group which is unsubstituted or which is substituted by one or more substituents as described herein.

According to some of any of the embodiments described herein, at least a portion of, or each peptide in, the plurality of aromatic dipeptides comprises a plurality of aromatic dipeptides of two aromatic amino acid residues as described herein.

According to some of any of the embodiments described herein, at least a portion of, or each peptide in, the plurality of aromatic dipeptides comprises aromatic homodipeptides, having two aromatic amino acid residues which are identical with respect to their side-chains residue, or in which the two aromatic amino acid residues are identical (the same).

Exemplary aromatic homodipeptides include, but are not limited to, phenylalanine-phenylalanine dipeptide, naphthylalanine-naphthylalanine dipeptide, (pentafluoro-phenylalanine)-(pentafluoro-phenylalanine) dipeptide, (iodo-phenylalanine)-(iodo-phenylalanine) dipeptide, (4-phenyl phenylalanine)-(4-phenyl phenylalanine) dipeptide and (p-nitro-phenylalanine)-(p-nitro-phenylalanine) dipeptide.

According to some of any of the embodiments described herein, each of the aromatic homodipeptides is a (substituted or unsubstituted) phenylalanine-phenylalanine dipeptide.

According to some of any of the embodiments described herein, each of the aromatic homodipeptides is an unsubstituted phenylalanine-phenylalanine dipeptide.

Herein throughout, "at least a portion" means at least 10%, at least 20%, at least 30%, at least 40%, at least 50%, at least 60%, at least 70%, at least 80%, at least 90%, at least 95%, at least 98%, or at least 99%.

In some embodiments, all of the aromatic dipeptides in the plurality of moieties forming the nanostructures are the same, that is, all have the same amino acid residues, and the same type of peptide bond linking therebetween.

According to embodiments of the present invention, at least a portion of, or each, aromatic dipeptide in the plurality of aromatic dipeptide type moieties forming the nanostructures, are end-capping modified aromatic dipeptides.

The phrase "end-capping modified aromatic dipeptide", as used herein, refers to an aromatic dipeptide as described herein in any of the respective embodiments which has been modified at the N-(amine)terminus and/or at the C-(carboxyl)terminus thereof.

The end-capping modification refers to the attachment of a chemical moiety to the terminus, so as to form a cap. Such a chemical moiety is referred to herein as an end-capping moiety and is typically also referred to herein and in the art, interchangeably, as a peptide protecting moiety or group.

The phrase "end-capping moiety", as used herein, refers to a moiety that when attached to the terminus of the peptide, modifies the end-capping. The end-capping modification typically results in masking the charge of the peptide terminus, and/or altering chemical features thereof, such as, hydrophobicity, hydrophilicity, reactivity, solubility and the like. Examples of moieties suitable for peptide end-capping modification can be found, for example, in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996).

Representative examples of N-terminus end-capping moieties include, but are not limited to, formyl, acetyl (also denoted herein as "Ac"), trifluoroacetyl, benzyl, benzyloxycarbonyl (also denoted herein as "Cbz"), tert-butoxycarbonyl (also denoted herein as "Boc"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "Fmoc"), and nitro-veratryloxycarbonyl ("NVOC").

Representative examples of C-terminus end-capping moieties are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus end-capping may be modified to an amide group.

Other end-capping modifications of peptides include replacement of the amine and/or carboxyl with a different moiety, such as hydroxyl, thiol, halide, alkyl, aryl, alkoxy, aryloxy and the like, as these terms are defined herein.

End-capping moieties can be classified by their aromaticity. Thus, end-capping moieties can be aromatic or non-aromatic.

Representative examples of non-aromatic end capping moieties suitable for N-terminus modification include, without limitation, formyl, acetyl trifluoroacetyl, tert-butoxycarbonyl, trimethylsilyl, and 2-trimethylsilyl-ethanesulfonyl. Representative examples of non-aromatic end capping moieties suitable for C-terminus modification include, without limitation, amides, allyloxycarbonyl, trialkylsilyl ethers and allyl ethers.

Representative examples of aromatic end capping moieties include, without limitation, fluorenylmethyloxycarbonyl (Fmoc), benzyl, benzyloxycarbonyl (Cbz), trityl and substituted trityl groups.

In a preferred embodiment of the present invention, the end-capping modified aromatic dipeptides are modified by an aromatic (e.g. Fmoc) end-capping moiety.

According to some of any of the embodiments described herein, the end-capping modified aromatic dipeptide is an end-capping modified homodipeptide.

According to some of any of the embodiments described herein, the end-capping modified homodipeptide is an end-capping modified diphenylalanine.

According to some of any of the embodiments described herein, the end-capping modified aromatic dipeptide is an N-terminus modified dipeptide.

According to some of any of the embodiments described herein, the end-capping modified aromatic dipeptide comprises an aromatic end capping moiety as described herein.

According to some of any of the embodiments described herein, the aromatic end capping moiety is Fmoc.

According to some of any of the embodiments described herein, at least a portion, or each, of the plurality of end-capping modified aromatic peptides type of aromatic moieties are aromatic homodipeptides modified at the N-terminus by an aromatic end-capping moiety.

According to some of any of the embodiments described herein, at least a portion, or each, of the plurality of end-capping modified aromatic peptides type of aromatic moieties are diphenylalanine (Phe-Phe or FF) modified at the N-terminus by an aromatic end-capping moiety. According to some of any of the embodiments described herein, at least a portion, or each, of the plurality of end-capping modified aromatic peptides type of aromatic moieties are Fmoc-Phe-Phe (Fmoc-FF).

According to some of any of the embodiments described herein, the plurality of aromatic moieties forming the fibrillar nanostructures further comprise a plurality of aromatic moieties of the type of halogenated aromatic amino acid, that is, an aromatic amino acid as defined herein, which comprises one or more halogen (halo) substituents on the aromatic group.

According to some of any of the embodiments described herein, the halogenated aromatic amino acid comprises in its side chain an aromatic moiety substituted by 1, 2, 3, 4, 5 or more (in case of an aromatic moiety of more than 6 carbon atoms) halogen substituents.

According to some of any of the embodiments described herein, at least a portion of, or each, of the halogenated aromatic amino acid moieties are fluorinated aromatic amino acids.

According to some of any of the embodiments described herein, the halogenated aromatic amino acid is a fluorinated aromatic amino acid, comprising 1, 2, 3, 4, 5 or more (in case of an aromatic moiety of more than 6 carbon atoms) fluoro substituents.

According to some of any of the embodiments described herein, in at least a portion of, or each, of the halogenated aromatic amino acid moieties, the aromatic amino acid is phenylalanine and the halogenated aromatic amino acid is a halogenated phenylalanine.

According to some of any of the embodiments described herein, in at least a portion of, or each, of the halogenated aromatic amino acid moieties, the aromatic amino acid is phenylalanine and the halogenated aromatic amino acid is a fluorinated phenylalanine.

According to some of any of the embodiments described herein, in at least a portion of, or each, of the halogenated aromatic amino acid moieties, the halogenated aromatic amino acid is pentafluorophenylalanine (F5-phenylalanine; F5-Phe; F5-F).

According to embodiments of the present invention, the halogenated amino acid moieties described herein are amine-modified aromatic amino acids, that is, the alpha amine of amino acid is substituted.

According to some of any of the embodiments described herein, in at least a portion of, or each, of the halogenated aromatic amino acid moieties, the amine-modified aromatic amino acid comprises an aromatic group attached to the alpha amine of the amino acid.

Any of the aromatic end-capping moieties as described herein for a dipeptide can be used as an aromatic group that substitutes the alpha amine of the halogenated amino acid.

The end-capping moieties described herein for N-terminus modification can also be utilized for providing an amine-modified halogenated aromatic amino acid as described herein.

According to some of any of the embodiments described herein, in at least a portion of, or each, of the halogenated aromatic amino acid moieties, the aromatic group substituting the alpha amine is Fmoc.

According to some of any of the embodiments described herein, at least a portion of, or each, of the amino-modified halogenated aromatic amino acid are Fmoc-modified halogenated aromatic amino acid, and in some embodiments, at least a portion of, or each, of the amino-modified halogenated aromatic amino acid are Fmoc-halogenated (e.g., fluorinated) phenylalanine.

According to some of any of the embodiments described herein, at least a portion of, or each, of the amino-modified halogenated aromatic amino acids are Fmoc-F5-Phe moieties.

According to some of any of the embodiments described herein, at least a portion of, or each, of the amino-modified halogenated aromatic amino acid are fluorinated phenylalanine, which comprise 1, 2, 3 or 4 fluoro substituents on the phenyl.

According to some of any of the embodiments described herein, at least a portion of, or each, of the amino-modified halogenated aromatic amino acid are fluorinated phenylalanines, which comprise two fluoro substituents on the phenyl.

According to some of any of the embodiments described herein, the hybrid hydrogel comprises a three-dimensional (3D) network of fibrillar structures formed of two or more types of aromatic moieties, a portion of the aromatic moieties being a plurality of aromatic homodipeptides each having an aromatic end-capping moiety (e.g., Fmoc) at the N-terminus thereof, and a portion of the aromatic moieties being a plurality of aromatic fluorinated amino acids having an aromatic group (e.g., Fmoc) attached to the alpha amine thereof.

According to some of any of the embodiments described herein, each of the fibrillar nanostructures is formed of the plurality of aromatic moieties as described herein in any of the respective embodiments.

According to some of any of the embodiments described herein, the hybrid hydrogel further comprises water or an aqueous solution.

According to some of any of the embodiments described herein, a total weight concentration of the plurality of aromatic moieties in the hydrogel (e.g., the two types of aromatic moieties) ranges from 1 mg/ml to 20 mg/ml, or from to 2 mg/ml to 20 mg/ml, or from 2 mg/ml to 15 mg/ml, or from 2 mg/ml to 10 mg/ml, or from 5 mg/ml to 10 mg/ml, including any intermediate value and subranges therebetween. According to some of any of the embodiments described herein, a total concentration of the aromatic moieties in the hydrogel is 1 mg/ml, or 2 mg/ml, or 3 mg/ml, or 4 mg/ml, or 5 mg/ml, or 6 mg/ml, or 7 mg/ml, or 8 mg/ml, or 9 mg/ml, or 10 mg/ml, or higher (e.g., up to 20 mg/ml).

According to some of any of the embodiments described herein, a molar ratio of the first type of aromatic moieties (end-capping modified aromatic dipeptides) and the second type of aromatic moieties (amino-modified halogenated aromatic amino acid) ranges from 10:1 to 1:10, or from 9:1 to 1:9, or from 8:1 to 1:8, or from 7:1 to 1:7, or from 6:1 to 1:6, or from 5:1 to 1:5, or from 4:1 to 1:4, or from 3:1 to 1:3, or from 2:1 to 1:2, or is 1:1, including any intermediate values and subranges therebetween.

According to some of any of the embodiments described herein, a weight concentration (e.g., mg/ml or weight %) ratio of the first type of aromatic moieties (end-capping modified aromatic dipeptides) and the second type of aromatic moieties (amino-modified halogenated aromatic amino acid) ranges from 10:1 to 1:10, or from 9:1 to 1:9, or from 8:1 to 1:8, or from 7:1 to 1:7, or from 6:1 to 1:6, or from 5:1 to 1:5, or from 4:1 to 1:4, or from 3:1 to 1:3, or from 2:1 to 1:2, or is 1:1, including any intermediate values and subranges therebetween.

According to some of any of the embodiments described herein, the fibrillar nanostructures formed of the plurality of aromatic moieties as described herein in any of the respective embodiments are self-assembled structures, which are formed upon contacting the plurality of aromatic moieties with an aqueous solution.

According to some of any of the embodiments described herein, the fibrillar nanostructures formed of the plurality of aromatic moieties as described herein in any of the respective embodiments are self-assembled nanostructures, which are formed upon contacting the plurality of aromatic moieties with an aqueous solution.

According to some of any of the embodiments described herein, in at least a portion, or in all, of the nanostructures forming the hybrid hydrogel, the at least two types of aromatic moieties as described herein are co-assembled to form the nanostructures, such that a nanostructure is composed of the two types of aromatic moieties.

According to some of any of the embodiments described herein, the hybrid hydrogel remains stable (e.g., no phase separation is observed) for at least 1 month, e.g., for 2, 3, 4, 5, 6 months or for a longer time period, at room temperature.

According to some of any of the embodiments described herein, the hybrid hydrogel features a stability (e.g., when maintained at room temperature for a tome period longer by at least 1 week than a hydrogel formed of a (self-assembled) plurality of amino-modified halogenated aromatic amino acid moieties alone.

According to some of any of the embodiments described herein, the hybrid hydrogel is characterized by a storage modulus, G', higher by at least 2-folds, or at least 3-folds, or at least 5-folds, and even 10-folds, 15-folds, about 20-folds or more, of a storage modulus of a hydrogel made of a (self-assembled) plurality of end-capping modified aromatic dipeptide moieties alone. According to some of any of the embodiments described herein, the hybrid hydrogel is characterized by a storage modulus, G', which is higher than the additive value of a storage modulus of a hydrogel made of a (self-assembled) plurality of end-capping modified aromatic dipeptide moieties and a storage modulus of a hydrogel made of a plurality of amine-modified halogenated aromatic amino acid moieties. That is, the effect of combining the two types of aromatic moieties on the storage modulus of the obtained hydrogel is synergistic.

According to some of any of the embodiments described herein, the hybrid hydrogel is characterized by a storage modulus, G', of at least 10,000, or at least 20,000, or at least 50,000, or at least 100,000, or at least 150,000 Pa.

According to some of any of the embodiments described herein, a molar ratio of the at least two types of aromatic moieties in the plurality of aromatic moieties determines a storage modulus, G', of the hydrogel and/or an average length of the fibrillar nanostructures formed of the plurality of aromatic moieties.

Thus, for example, in some embodiments, at a molar ratio of 1:1, the hybrid hydrogel features a storage modulus, G', higher than 100,000 Pa. At a molar ratio of 3:1 the hybrid hydrogel features a storage modulus, G', higher than 20,000 Pa, or even higher than 50,000 Pa. At a molar ratio of 1:3, the hybrid hydrogel features a storage modulus higher than 10,000 Pa, or even higher than 15,000 Pa.

According to some of any of the embodiments described herein, the hybrid hydrogel is transparent.

According to an aspect of some embodiments of the present invention there is provided a process of preparing the hydrogel hybrid as described herein, the process comprising contacting a first solution comprising the end-capping modified aromatic dipeptide and a first organic solvent, at least a second solution comprising the amine-modified halogenated aromatic amino acid and a second organic solvent, and an aqueous solution, thereby preparing the hybrid hydrogel.

In some embodiments, the first and second solvents are water-miscible solvents and can be the same or different.

Examples of water-miscible organic solvents include, without limitation, simple alcohols, such as, methanol, ethanol, 1-propanol, 2-propanol, 1-butanol, 2-butanol, 2-methyl-1-propanol, 2-methyl-2-propanol, 2,2-dimethyl-1-propanol and their halogen substituted analogues, ethylene glycol, acetone, dimethylsulfoxide (DMSO), acetic acid diethyl ether, tetrahydrofurane etc.

In some embodiments, the first organic solvent is DMSO.

In some embodiments, the second organic solvent is ethanol.

In some embodiments, the second organic solvent is DMSO.

According to some of any of the embodiments described herein, a total concentration of the end-capping modified aromatic dipeptide and the amine-modified halogenated aromatic amino acid in the aqueous solution ranges from 0.1 mg/ml to 20 mg/ml, or from 1 mg/ml to 20 mg/ml, or from 1 mg/ml to 15 mg/ml, or from 1 mg/ml to 10 mg/ml, or is 5 mg/ml, including any intermediate values and subranges therebetween.

According to some of any of the embodiments described herein, the hybrid hydrogel is formed within minutes (e.g., from 1 to 60, or from 1 to 40, or from 1 to 30, or from 1 to 20, or from 2 to 10 minutes, including any intermediate values and subranges therebetween) upon the contacting the plurality of aromatic moieties with the aqueous solution.

According to some of any of the embodiments described herein, the aqueous solution is water.

According to some of any of the embodiments described herein, the contacting is effected at room temperature.

According to an aspect of some embodiments of the present invention there is provided a process of preparing the hybrid hydrogel of the present embodiments, essentially as described herein.

According to an aspect of some embodiments of the present invention there is provided an article-of-manufacturing, comprising the hybrid hydrogel as described herein in any of the respective embodiments.

The article-of-manufacture can be, for example, a cell culture matrix, a protein microarray chip, a biosensor, a medicament, a drug delivery system, a cosmetic or cosmeceutical agent, an implant, an artificial body part, a tissue engineering and regeneration system, and a wound dressing, as well as various medical devices.

The beneficial characteristics of the hydrogels described herein render them highly suitable for use in various applications. Thus, each of the hydrogels, composition-of-matters or compositions described herein can be utilized for forming an article-of-manufacture, whereby the article-of-manufacture can be, for example, a cell culture matrix, a protein microarray chip, a biosensor, a medicament, a drug delivery system, a cosmetic or cosmeceutical agent, an implant, an artificial body part, a tissue engineering and regeneration system, and a wound dressing, as well as various medical devices.

Herein, the phase "cell culture matrix" refers to biocompatible natural and synthetic matrix that can be used to create defined three-dimensional (3D) microenvironment which allows cell growth. The matrix optimally mimics the natural environment of the cells. Cell culture matrices are often used in tissue engineering.

The hybrid hydrogels described herein are also highly suitable as matrices for stem cell differentiation.

As used herein, the phrase "protein microarray chip" refers to a solid base, e.g., pieces of glass, on which different molecules of protein have been affixed at separate locations in an ordered manner, thus forming a microscopic array. In general, microarray chips are measurement devices used in biomedical applications to determine the presence and/or amount of proteins in biological samples. Other applications include, for example, the identification of protein-protein interactions, of substrates of protein kinases, or of targets of biologically active small molecules. Another use is as a base for antibodies, where the antibodies are spotted onto the protein chip and used as capture molecules to detect proteins from cell lysate solutions. As will be familiar to one ordinarily skilled in the art, the formation of high-density protein chips to fully understand protein function had previously been a tremendous challenge. This is because proteins need to be in a wet environment in order to remain structurally intact and carry out their biological functions. Since hydrogels allow the proteins to remain in a wet environment as described hereinabove, it is highly advantageous to use hydrogels in forming protein microarray chips.

Herein the term "biosensor" refers to a device that combines a biological component with a physicochemical detector component and which is utilized for the detection of an analyte.

As used herein, the term "medicament" refers to a licensed drug taken to cure or reduce symptoms of an illness or medical condition.

As used herein, the phrase "drug delivery system" refers to a system for transportation of a substance or drug to a specific location, and more specifically, to a desired bodily target, whereby the target can be, for example, an organ, a tissue, a cell, or a cellular compartment such as the nucleus, the mitochondria, the cytoplasm, etc. This phrase also refers to a system for a controlled release of a substance or drug at a desired rate.

As used herein, the term "implant" refers to artificial devices or tissues which are made to replace and act as missing biological structures. These include, for example, dental implants, artificial body parts such as artificial blood vessels or nerve tissues, bone implants, and the like.

As used herein, the phrase "tissue engineering and regeneration" refers to the engineering and regeneration of new living tissues in vitro, which are widely used to replace diseased, traumatized or other unhealthy tissues.

As used herein, the phrase "cosmetic or cosmeceutical agent" refers to topical substances that are utilized for aesthetical purposes. Cosmeceutical agents typically include substances that further exhibit therapeutic activity so as to provide the desired aesthetical effect. Cosmetic or cosmeceutical agents in which the hydrogels, compositions-of-matter and compositions described herein can be beneficially utilized include, for example, agents for firming a defected skin or nail, make ups, gels, lacquers, eye shadows, lip glosses, lipsticks, and the like.

Medical devices in which the hydrogels, compositions-of-matter and compositions described herein can be beneficially utilized include, for example, anastomotic devices (e.g., stents), sleeves, films, adhesives, scaffolds and coatings.

Anastomosis is the surgical joining of two organs. It most commonly refers to a connection which is created between tubular organs, such as blood vessels (i.e., vascular anastomosis) or loops of intestine. Vascular anastomosis is commonly practiced in coronary artery bypass graft surgery (CABG), a surgical procedure which restores blood flow to ischemic heart muscle in which blood supply has been compromised by occlusion or stenosis of one or more of the coronary arteries.

Stents comprising the hydrogels, compositions-of-matter or compositions described herein can be used, for example, as scaffolds for intraluminal end to end anastomoses; as gastrointestinal anastomoses; in vascular surgery; in transplantations (heart, kidneys, pancreas, lungs); in pulmonary airways (trachea, lungs etc.); in laser bonding (replacing sutures, clips and glues) and as supporting stents for keeping body orifices open.

Sleeves comprising the hydrogels, compositions-of-matter or compositions described herein can be used, for example, as outside scaffolds for nerves and tendon anastomoses.

Films comprising the hydrogels, compositions-of-matter or compositions described herein can be used, for example, as wound dressing, substrates for cell culturing and as abdominal wall surgical reinforcement.

Coatings of medical devices comprising the hydrogels, compositions-of-matter or compositions described herein can be used to render the device biocompatible, having a therapeutic activity, a diagnostic activity, and the like.

Other devices include, for example, catheters, aortic aneurysm graft devices, a heart valve, indwelling arterial catheters, indwelling venous catheters, needles, threads, tubes, vascular clips, vascular sheaths and drug delivery ports.

Other potential non pharmaceutical applications of the hydrogel of the present invention are related to the exceptional material properties of the hydrogel. These applications include, for example, employing the hydrogel in a vibration-damping device or in a packaging material.

As used herein, the term "vibration-damping device" refers to a device which tends to reduce the amplitude of oscillations. Applications include for example the reduction of electric-signal (and hence sound) distortion in audio-electrical devices.

As used herein, the term "packaging material" refers to material designated for the enclosing of a physical object, typically a product which needs physical protection.

By being composed of peptide building blocks, the hydrogels described herein are further biocompatible and are therefore highly suitable for use in medical applications, as is detailed herein.

The hybrid hydrogel according to the present embodiments can be utilized as a matrix for encapsulating therein or attaching thereto various agents.

Hence, according to another aspect of the present invention there is provided a composition-of-matter, which comprises the hybrid hydrogel described herein and at least one agent being attached thereto or encapsulated therein.

Agents that can be beneficially encapsulated in or attached to the hybrid hydrogel include, for example, therapeutically active agents, diagnostic agents, biological substances and labeling moieties. More particular examples include, but are not limited to, drugs, cells, proteins, enzymes, hormones, growth factors, nucleic acids, organisms such as bacteria, fluorescence compounds or moieties, phosphorescence compounds or moieties, and radioactive compounds or moieties.

As used herein, the phrase "therapeutically active agent" describes a chemical substance, which exhibits a therapeutic activity when administered to a subject. These include, as non-limiting examples, inhibitors, ligands (e.g., receptor agonists or antagonists), co-factors, anti-inflammatory drugs (steroidal and non-steroidal), anti-psychotic agents, analgesics, anti-thrombogenic agents, anti-platelet agents, anti-coagulants, anti-diabetics, statins, toxins, antimicrobial agents, anti-histamines, metabolites, anti-metabolic agents, vasoactive agents, vasodilator agents, cardiovascular agents, chemotherapeutic agents, antioxidants, phospholipids, anti-proliferative agents and heparins.

As used herein, the phrase "biological substance" refers to a substance that is present in or is derived from a living organism or cell tissue. This phrase also encompasses the organisms, cells and tissues. Representative examples therefore include, without limitation, cells, amino acids, peptides, proteins, oligonucleotides, nucleic acids, genes, hormones, growth factors, enzymes, co-factors, antisenses, antibodies, antigens, vitamins, immunoglobulins, cytokines, prostaglandins, vitamins, toxins and the like, as well as organisms such as bacteria, viruses, fungi and the like.

As used herein, the phrase "diagnostic agent" describes an agent that upon administration exhibits a measurable feature that corresponds to a certain medical condition. These include, for example, labeling compounds or moieties, as is detailed hereinunder.

As used herein, the phrase "labeling compound or moiety" describes a detectable moiety or a probe which can be identified and traced by a detector using known techniques such as spectral measurements (e.g., fluorescence, phosphorescence), electron microscopy, X-ray diffraction and imaging, positron emission tomography (PET), single photon emission computed tomography (SPECT), magnetic resonance imaging (MRI), computed tomography (CT) and the like.

Representative examples of labeling compounds or moieties include, without limitation, chromophores, fluorescent compounds or moieties, phosphorescent compounds or moieties, contrast agents, radioactive agents, magnetic compounds or moieties (e.g., diamagnetic, paramagnetic and ferromagnetic materials), and heavy metal clusters, as is further detailed hereinbelow, as well as any other known detectable moieties.

As used herein, the term "chromophore" refers to a chemical moiety or compound that when attached to a substance renders the latter colored and thus visible when various spectrophotometric measurements are applied.

A heavy metal cluster can be, for example, a cluster of gold atoms used, for example, for labeling in electron microscopy or X-ray imaging techniques.

As used herein, the phrase "fluorescent compound or moiety" refers to a compound or moiety that emits light at a specific wavelength during exposure to radiation from an external source.

As used herein, the phrase "phosphorescent compound or moiety" refers to a compound or moiety that emits light without appreciable heat or external excitation, as occurs for example during the slow oxidation of phosphorous.

As used herein, the phrase "radioactive compound or moiety" encompasses any chemical compound or moiety that includes one or more radioactive isotopes. A radioactive isotope is an element which emits radiation. Examples include α-radiation emitters, β-radiation emitters or γ-radiation emitters.

While a labeling moiety can be attached to the hybrid hydrogel, it is noted that the end-capping moieties composing at least a portion of the aromatic moieties can serve as a labeling moiety per se.

Thus, for example, in cases where the Fmoc group described hereinabove is used as the end-capping moiety, the end-capping moiety itself is a fluorescent labeling moiety.

In another example, wherein the Fmoc described hereinabove further includes a radioactive fluoro atom (e.g., $^{18}$F) is used as the end-capping moiety, the end-capping moiety itself is a radioactive labeling moiety.

Other materials which may be encapsulated by the hybrid hydrogel of the present invention include, without limitation, conducting materials, semiconducting materials, thermoelectric materials, magnetic materials, light-emitting materials, biominerals, polymers and organic materials.

Each of the agents described herein can be attached to or encapsulated in the hydrogel by means of chemical and/or physical interactions. Thus, for example, compounds or moieties can be attached to the external and/or internal surface of the hydrogel, by interacting with functional groups present within the hydrogel via, e.g., covalent bonds, electrostatic interactions, hydrogen bonding, van der Waals interactions, donor-acceptor interactions, aromatic (e.g., π-π interactions, cation-π interactions and metal-ligand interactions. These interactions lead to the chemical attachment of the material to the fibrous network of the hybrid hydrogel.

As an example, various agents can be attached to the hybrid hydrogel via chemical interactions with the side chains, N-terminus or C-terminus of the aromatic amino acids or peptides composing the hydrogel and/or with the end-capping moieties.

Alternatively, various agents can be attached to the hybrid hydrogel by physical interactions such as magnetic interactions, surface adsorption, encapsulation, entrapment, entanglement and the likes.

Attachment of the various agents to the hybrid hydrogel can be effected either prior to or subsequent to the hydrogel formation. Thus, for example, an agent or moiety can be attached to one or more of the aromatic moieties composing the hydrogel prior to the hydrogel formation, resulting in a hydrogel having the agent attached thereto. Alternatively, an agent or moiety can be attached to surface groups of the hybrid hydrogel upon its formation.

Encapsulation, entrapment, or entanglement of the various agents is typically effected by forming the hybrid hydrogel in a solution containing the encapsulated agent.

Hydrogels entrapping therein a biological or chemical agent can be beneficially utilized for encapsulation and controlled release of the agent.

Hydrogels having a labeling moiety attached thereto or encapsulated therein can be utilized in a variety of applications, including, for example, tracing and tracking the location of the fibrous networks of the present invention in mechanical devices and electronic circuitry; and tracing, tracking and diagnosing concentrations of the hydrogels of the present invention in a living tissue, cell or host.

As is further detailed in the Examples section that follows, it has been shown that the hydrogel described herein can be utilized as a highly efficient cell culture matrix, allowing for the adhesion of cells thereto while maintaining the cells viability, morphology and proliferation rate.

Hence, by being remarkably rigid, stable, biocompatible and further by being readily subjected to chemical and physical manipulations that allow the attachment thereto or the encapsulation therein of various agents, the hybrid hydrogels and composition-of-matters described herein can be beneficially utilized in various applications, as is detailed hereinunder. The hybrid hydrogels or composition-of-matters described herein can, for example, form a part of a pharmaceutical, cosmetic or cosmeceutical compositions, either alone or in the presence of a pharmaceutically or cosmetically acceptable carrier.

As used herein, a "pharmaceutical, cosmetic or cosmeceutical composition" refers to a preparation of the hydrogel or the composition-of-matter described herein, with other chemical components such as acceptable and suitable carriers and excipients. The purpose of a pharmaceutical composition is to facilitate administration of a compound to an organism. The purpose of a cosmetic or cosmeceutical composition is typically to facilitate the topical application of a compound to an organism, while often further providing the preparation with aesthetical properties.

Hereinafter, the term "pharmaceutically, cosmetically or cosmeceutically acceptable carrier" refers to a carrier or a diluent that does not cause significant irritation to an organism and does not abrogate the biological activity and properties of the applied compound. Examples, without limitations, of carriers include propylene glycol, saline, emulsions and mixtures of organic solvents with water, as well as solid (e.g., powdered) and gaseous carriers.

The compositions described herein may be formulated in conventional manner using one or more acceptable carriers comprising excipients and auxiliaries, which facilitate processing of the hydrogel into preparations. Proper formulation is dependent upon the route of administration chosen.

Techniques for formulation and administration of drugs may be found in "Remington's Pharmaceutical Sciences," Mack Publishing Co., Easton, PA, latest edition.

The pharmaceutical compositions described herein can be formulated for various routes of administration. Suitable routes of administration may, for example, include oral, sublingual, inhalation, rectal, transmucosal, transdermal, intracavemosal, topical, intestinal or parenteral delivery, including intramuscular, subcutaneous and intramedullary injections as well as intrathecal, direct intraventricular, intravenous, intraperitoneal, intranasal, or intraocular injections.

Formulations for topical administration include but are not limited to lotions, ointments, gels, creams, suppositories, drops, liquids, sprays and powders. Conventional carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The compositions may, if desired, be presented in a pack or dispenser device, such as an FDA (the U.S. Food and Drug Administration) approved kit, which may contain the hydrogel. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

Peptides and Molecules:

Lyophilized peptides Fmoc-Phe-Phe-OH and Fmoc-F5-Phe-OH were purchased from Bachem (Budendorf, Switzerland) and Sigma Aldrich (Rehovot, Israel), respectively, and were used without further purification.

Gel Preparation:

The stock solution of the Fmoc-FF peptide was prepared by dissolving the lyophilized peptide powder in DMSO (dimethyl sulfoxide) to a concentration of 100 mg/ml. The stock solution of the Fmoc-F5-Phe peptide was prepared by dissolving the lyophilized peptide powder in ethanol to a concentration of 10 mg/ml. The peptides stock solutions were mixed at the required ratios and diluted in DDW to a final concentration of 5 mg/ml.

Rheology:

The in-situ kinetics of hydrogel formation and mechanical properties were characterized by an AR-G2 rheometer (TA Instruments, USA). Time-sweep oscillatory tests in 20 mm parallel-plate geometry were conducted on 230 µl of fresh solution (resulting in a gap size of 0.6 mm) at room temperature. In order to determine the linear viscoelastic region, at which the time sweep oscillatory tests were performed, oscillatory strain (0.01-100%) and frequency sweeps (0.01-100 Hz) were conducted 1 hour after attaching the sample to the rheometer (soak time). G' and G", the storage and loss moduli, respectively, were obtained at 5 Hz oscillation and 0.5% strain deformation for each sample. All rheological measurements were conducted at a final peptide concentration of 5 mg/ml.

Transmission Electron Microscopy (TEM):

The samples were prepared for TEM analysis by applying 10 µl samples to a 400-mesh copper grids (Electron Microscopy Sciences LTD). The excess liquid was removed 2 minutes later. Samples were examined using a JEOL 1200EX electron microscope (JEOL), operating at 80 kV.

Fluorescence Spectroscopy:

The emission spectra of the gels were recorded using a Horiba Jobin Yvon FL3-11 fluorimeter (Horiba Jobin Yvon, NJ, USA). A quartz cuvette with an optical path length of 1 cm was used. The gels where assembled within the cuvette and the spectrum was monitored a few minutes following dilution. The experiments were carried out using an excitation wavelength of 280 nm and 5-nm excitation and emission slits.

Example 1

Hybrid Hydrogel Formation

In spite of the interesting properties of Fmoc-F5-Phe hydrogel, its rigidity and durability are inferior as compared to other biomolecular hydrogel. In light of the need to stabilize this hydrogel, the present inventors have conceived harnessing the mechanical properties of Fmoc-FF hydrogels and have studied the formation of hybrid assemblies.

FIG. 1A presents the molecular structures of Fmoc-FF and Fmoc-F5-Phe, and FIG. 1B presents a schematic presentation of the tested gelation process of each of the building block separately and of a hybrid hydrogel formed of the two peptides.

The Fmoc-FF hydrogels were prepared using the solvent-switch method (Mahler et al. *Adv. Mater.* 18, 1365-1370, (2006)), by dissolving the peptide in DMSO and then diluting the stock solution in water. Following dilution, a rigid hydrogel was formed, as schematically shown in FIG. 1B. Fmoc-F5-Phe hydrogel was also prepared by the solvent-switch method, by first dissolving it in ethanol and then diluting it in water. Similarly, the water dilution resulted in the formation of a hydrogel, as schematically shown in FIG. 1B.

Hybrid hydrogels were prepared using the two building blocks, Fmoc-F5-Phe and FmocFF, at three stoichiometric ratios of 3:1, 1:1 and 1:3 by mixing both building-block stock solutions, then diluting them into water.

FIGS. 1C and 1D present images of the hydrogels obtained in the tested gelation processes. FIG. 1C presents images of inverted tubes of (left to right) Fmoc-F5-Phe, Fmoc-F5-Phe/Fmoc-FF 3:1, 1:1, 1:3, respectively, and Fmoc-FF. FIG. 1D presents images of inverted tubes of Fmoc-F5-Phe (right) and 1:1 hybrid hydrogel (left), three weeks after preparation.

A shown in FIG. 1C, in all cases, a transparent homogenous hydrogel was formed. As shown in FIG. 1D, the Fmoc-F5-Phe formed a hydrogel, however after seven days the hydrogel collapsed and a phase separation was observed.

The stability of the hybrid hydrogels was monitored over a period of 6 months, and in all cases, a stable 3D structure was maintained, as shown in FIG. 1D.

The gelation kinetics of the formed hydrogels was then tested, and images of the tubes, taken at 1-minute intervals, are presented in FIG. 2, showing the transition from a cloudy mixture to a transparent hydrogel.

As shown in FIG. 2, while Fmoc-F5-Phe hydrogel formation occurred within seconds, the formation of a transparent rigid hydrogel by Fmoc-FF occurred only after about 4 minutes. The 3:1 and 1:3 hybrid hydrogels showed similar kinetics to that of Fmoc-FF, with a solid and transparent hydrogel forming after 5 minutes. A shorter gelation duration was observed for the 1:1 ratio hybrid, forming about 2 minutes after preparation.

Example 2

Hybrid Hydrogel Characterization

The hydrogel underlying morphology was studied using transmission electron microscopy (TEM) analysis. TEM samples of all five hydrogel variants, namely the hybrid hydrogels and the two individual hydrogels, were prepared at a concentration of 5 mg/mL, immediately after diluting the stock solutions in water.

FIGS. 3A-E present the TEM structural analyses of Fmoc-F5-Phe-OH (FIG. 3A); of the hybrid hydrogels 3:1, 1:1 and 1:3, (FIGS. 3B, 3C and 3D, respectively); and of Fmoc-FF (FIG. 3E).

As shown therein, in all cases, fibrils with width in the range of 15-25 nm were detected. For the Fmoc-FF and Fmoc-F5-Phe hydrogels, tangled, several microns-long fibrils could be seen, while for all hybrid hydrogels short and less tangled fibrils were manifested. Surprisingly, the 1:1 hybrid hydrogel contained fibrils that were shorter than those of all the other hydrogels, with a length of only a few microns.

In addition, to confirm the presence of fluorine in the fibrils of all hybrid hydrogels, energy-dispersive X-ray spectroscopy (EDS) analyses were performed, and the obtained data are presented in FIG. 3F. As shown therein, in all cases, fluorine was indeed detected, suggesting that the fibrils are indeed composed of the two building blocks.

The mechanical properties of the various hydrogels were monitored using rheological analysis. These measurements can also shed light on the kinetics of hydrogel formation. Strain Sweep (at 5 Hz frequency) and Frequency Sweep (at 0.5% strain) oscillatory measurements were performed in order to optimize the appropriate measurement conditions. The obtained data is presented in FIGS. 4A-F.

FIGS. 4A and 4B present the data obtained for the 1:1 hybrid hydrogel at 25° C. Similar results were obtained for the other hydrogels, and the conditions for time sweep measurements were thus set to be 0.5% Strain and 5 Hz Frequency.

FIG. 4C presents the rheological analysis of the formed hydrogels and shows that a significant portion of the gel rigidification is achieved within less than 6 minutes, whereby the completion of the gelation process and the final rigidification, i.e. the time in which the storage modulus G' reaches its plateau, is a lengthier process. The data presented in FIG. 4C further show that the individual Fmoc-FF hydrogel exhibits high rigidity, with a G' value of more than 9 kPa and a short gelation time of approximately 10 minutes. The Fmoc-F5-Phe hydrogel reached a G' value of approximately 3.5 kPa after 2 hours, yet it continued to rise slowly, reaching a value of 4.2 kPa after 3 hours. A possible explanation for this phenomenon is the slow diffusion of the building block in the process of structural organization into fibers within a viscous solution, as the Fmoc-F5-Phe solution became very viscous immediately following dilution in water while the Fmoc-FF solution remained in a liquid state for a few minutes.

As further shown in FIG. 4C, the storage modulus of the 3:1 hybrid hydrogel reached a plateau within 6 minutes with a G' value of approximately 22.5 kPa. The storage modulus of the 1:3 hybrid hydrogel reached a plateau after about 50 minutes with a G' value of approximately 68.8 kPa. Strikingly, the 1:1 hybrid hydrogel reached a plateau after 40 minutes with a considerably higher storage modulus close to 190 kPa. Notably, the final storage moduli of all hybrids were higher than those of the pure gels, reaching their plateau after 60 minutes.

FIG. 4D presents a bar graph showing the storage modulus of the obtained hydrogels. The respective data is also presented in Table 1 below. The mechanical properties of the 1:1 hybrid hydrogel are extraordinary, with a very high storage modulus value, placing this hydrogel as one of the most rigid supramolecular hydrogel reported to date. This high mechanical rigidity along with its tunable ability by forming various hybrid hydrogel ratios is of particular interest in tissue engineering and cell culture applications, where the nanoscale morphological and mechanical environment is vital for controlling of stem cell differentiation.

Recently, it has been shown that stem cells can go stiffness-directed fate selection on soft (1 kPa), stiff (13 kPa) and rigid (32 kPa) hydrogels into neuronal, chondrogenic, and osteogenic differentiation respectively. See, for example, Wang, P.-Y. et al. *Adv. Funct. Mater.* 22, 3414-3423, (2012); and Alakpa, E. V. et al. *Chem* 1, 298-319, (2016). The extraordinary rigid hydrogel presented herein (190 kPa) can serve as new scaffolds for stem cell differentiation.

TABLE 1

| Type of Biomaterial | Rheology (kPa) 25° C. | Gelation Time post mixing* | Shelf Life |
| --- | --- | --- | --- |
| Fmoc-F$_5$-Phe-OH | 3.5 | 3 hours | 2 weeks |
| Hybrid of 25/75 w/w (1:3); 0.5% | 68.8 | 50 minutes | More than 6 month |
| Hybrid of 50/50 w/w (1:1); 0.5% | 190 | 40 minutes | More than 6 month |
| Hybrid of 75/25 w/w (3:1); 0.5% | 22.5 | 6 minutes | More than 6 month |
| FmocFF 0.5% | 9 | 10 minutes | More than 6 month | kPa = 1000 × Pascal
*Geleation time was determined at the highest G' value

To further probe the internal organization of the hybrid hydrogels, the fluorescence spectra at the near-UV region was monitored. In this spectral range the Fmoc aromatic moiety, which is common to both building blocks, exhibits characteristic fluorescence emission [Fichman et al. *Cryst Eng Comm* 17, 8105-8112, (2015)].

The obtained data is presented in FIG. 4E, and show that all the hydrogels feature an emission peak at 320 nm. However, the 1:1 hybrid hydrogel spectra presented a second, more intense peak at 360 nm. The spectra of both the 1:3 and 3:1 hybrids hydrogels also presented increased emission at 360 nm, yet it manifested in combination with the 320 nm peak.

These results suggest that new aromatic interactions arise in the hybrid hydrogels as compared to the individual hydrogels, further indicating that the hybrid hydrogels are formed through co-assembly of the two building blocks.

FIG. 4F presents the time-dependent fluorescence emission of the 1:1 hybrid hydrogel and shows that at 6 minutes after the initiation of gelation, the fluorescence pattern is similar to that of either of the individual hydrogel with a single peak at 320 nm, while the 360 nm peak is emerging at later time points, concomitantly with the gelation kinetics. This further supports the notion that new molecular interactions arise as the result of a co-assembly process.

The extraordinary rigidity of the hybrid Fmoc-F5-Phe/Fmoc-FF hybrid hydrogels described herein in one of the highest rigidities ever reported for supramolecular hydrogels. FIG. 5 compares the storage moduli of different classes of previously reported hydrogels, namely synthetic (green region), including chitosan crosslinked with glutaraldehyde, thiol modified hyaluronic acid, Fmoc-FF and polyacrylamide gels, natural orange region), which includes collagen, and hybrid gels (yellow region), such as chitosan/PEG, Fmoc-FF/alginate, hyaluronic acid/fibrinogen and the storage modulus of the Fmoc-F5-Phe/Fmoc-FF hybrid gels described herein (blue region).

Example 3

Additional Hybrid Hydrogels
Materials:

Lyophilized powders of Fmoc-3,4-difluoro-L-phenylalanine (Fmoc-3,4-diF-Phe) and Fmoc-3,5-difluoro-L-phenylalanine (Fmoc-3,5-diF-Phe) were purchase from Chem-Impex INT'L inc. and Fmoc-Phe-Phe-OH (FmocFF) was purchased from Bachem (Budendorf, Switzerland). All powders were used without further purification.

Formation of the Hydrogels:

Fmoc-FF, Fmoc-3,4-diF-Phe and Fmoc-3,4-diF-Phe stock solutions were prepared separately by dissolving the powders to a concentration of 100 mg/mL in dimethyl sulfoxide (DMSO) and vortexed until the solution became transparent. Single peptide solutions were prepared by adding 50 μL of stock solutions to 950 μL double distilled water and immediately vortexed. FmocFF: Fmoc-diF-Phe co-assembled solutions at a final concentration of 5 mg/ml were prepared by combining the two peptides stock solutions in DMSO at the desired molar ratios of 3:1 (37.5 μL and 12.5 μL), 1:1 (25 μL and 25 μL) and 1:3 (12.5 μL and 37.5 μL), respectively. The co-assembled solutions were then diluted in 950 μL double distilled water and vortexed. The gels were formed upon 30-60 minutes.

Characterization:

FIG. 6 presents TEM images of hydrogels formed of Fmoc-FF, Fmoc-(3,4-diF)-Phe and of hybrid hydrogels formed at 3:1, 1:1 and 1:3 molar ratios of these aromatic moieties.

FIG. 7 presents TEM images of hydrogels formed of Fmoc-FF, Fmoc-(3,4-diF)-Phe and of hybrid hydrogels formed at 3:1, 1:1 and 1:3 molar ratios of these aromatic moieties.

Similarly to the hybrid hydrogels described in Examples 1 and 2 above, the fibrillar structures forming the hybrid hydrogels were shown to be shorter in length and less entangled, compared to the structures formed of Fmoc-FF alone.

Example 4

Cell Viability Tests

In order to exploit whether the hybrid hydrogel described herein can serve as a scaffold for tissue engineering applications, its biocompatibility was examined using cellular in vitro experiments.

After gelation (in 20 ml vials) the hybrid hydrogels were aged at room temperature for 24 hours without disturbance and were thereafter washed with DMEM growth medium (pen-strep, serum 1-glu) 3 times for 1 hour each on an orbital shaker.

Bioadhesive extract was performed by adding culture medium (DMEM) to the washed gels at a concentration of 0.2 gram/ml and incubation for 24 hours in an incubator (37° C., 5% $CO_2$).

3T3-mouse fibroblast cells were purchased from ATCC and cultured in Dulbecco's modified Eagle's medium (DMEM) supplemented with 10% fetal calf serum, 100 U mL-1 penicillin, 100 U mL-1 streptomycin, and 2 mmol L-1 L-glutamine (all from Biological Industries, Israel). The cells were maintained in a Petri dish at 37° C. in a humidified atmosphere containing 5% $CO_2$. After reaching a confluence of 90%, the cells were separated from the Petri dish using a "trypsin A" solution and were seeded into 96-well plates at concentrations of 20,000 cells per well with 0.1 ml of fresh culture medium and incubated for 24 hours. In the next step the medium was removed and replaced with 0.1 ml per well of bioadhesive extract medium.

MTT test of 3T3 cells (fibroblast) after 24 hours treatment with bioadhesive extract medium was performed. 20 mL of a MTT solution (5 mg/mL) in phosphate buffer saline (PBS) was added to each well. After 4 hours incubation, 100 mL of DMSO was added to extract the MTT reduced adduct (Formazan). All the samples were shaken for 20 minutes to allow a complete dissolution of the precipitated Formazan in DMSO. Absorbance was measured using a Tecan Spark plate reader at 570 nm. Background was measured at 680 nm.

FIG. 8 presents the viability of the cells, expressed as percentage, compared to a control medium lacking the hydrogels. As shown therein, all hydrogels promoted cell growth and viability to at least the same extent as the control, and mostly to a higher extent, indicating the biocompatibility of the hydrogels and their suitability to serve as an effective matrix for cell growth.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A hybrid hydrogel comprising a three-dimensional network of fibrillar nanostructures, at least a portion of said fibrillar nanostructures being formed of a plurality of aromatic moieties, said plurality of aromatic moieties comprising at least two different types of aromatic moieties, at least one type of said aromatic moieties being an N-terminus modified aromatic homodipeptide that comprises an aromatic end-capping moiety, and at least one type of said aromatic moieties being a halogenated aromatic amino acid that further comprises an aromatic moiety attached to the alpha amine of said amino acid, wherein the hybrid hydrogel is characterized by a storage modulus, G', at a total concentration of the plurality of aromatic moieties of 0.5% by weight, higher by at least 2-folds, of a storage modulus of a hydrogel made of said N-terminus modified aromatic homodipeptide at a concentration of 0.5% by weight; and wherein a ratio of said N-terminus modified aromatic homodipeptide to said halogenated aromatic amino acid that further comprises an aromatic moiety attached to the alpha amine of said amino acid ranges from 3:1 to 1:3.

2. The hybrid hydrogel of claim 1, wherein an average length of said fibrillar nanostructures formed of said plurality of aromatic moieties is lower than 10 microns.

3. The hybrid hydrogel of claim 1, characterized by a storage modulus, G', higher by at least 3-folds, of a storage modulus of a hydrogel made of said N-terminus modified aromatic homodipeptide.

4. The hybrid hydrogel of claim 1, characterized by a storage modulus, G', of at least 20,000 Pa.

5. The hybrid hydrogel of claim 1, wherein a molar ratio of said at least two types of aromatic moieties in said plurality of aromatic moieties determines a storage modulus, G', of the hydrogel and/or an average length of said fibrillar nanostructures formed of said plurality of aromatic moieties.

6. The hybrid hydrogel of claim 1, wherein each of said fibrillar nanostructures is formed of said plurality of aromatic moieties.

7. The hybrid hydrogel of claim 1 wherein said N-terminus modified aromatic homodipeptide is an N-terminus modified diphenylalanine.

8. The hybrid hydrogel of claim 1, wherein said aromatic end-capping moiety is Fmoc (fluorenylmethyloxycarbonyl).

9. The hybrid hydrogel of claim 1, wherein said halogenated aromatic amino acid comprises in its side chain an aromatic moiety substituted by 1, 2, 3, 4, 5 or more halogen substituents.

10. The hybrid hydrogel of claim 1, wherein said halogenated aromatic amino acid is a fluorinated aromatic amino acid.

11. The hybrid hydrogel of claim 1, wherein said halogenated aromatic amino acid is a halogenated phenylalanine.

12. The hybrid hydrogel of claim 11, wherein said halogenated aromatic amino acid is a fluorinated phenylalanine which comprises 1, 2, 3, 4, 5 or more fluoro substituents.

13. The hybrid hydrogel of claim 1, wherein said halogenated aromatic amino acid is F5-phenylalanine (pentafluorophenylalanine).

14. The hybrid hydrogel of claim 1, wherein said aromatic moiety attached to the alpha amine of said amino acid is Fmoc (fluorenylmethyloxycarbonyl).

15. An article-of-manufacturing, comprising the hybrid hydrogel of claim 1.

* * * * *